US006531137B2

(12) United States Patent
Guertler et al.

(10) Patent No.: US 6,531,137 B2
(45) **Date of Patent: *Mar. 11, 2003**

(54) RETROVIRUS FROM THE HIV GROUP AND ITS USE

(75) Inventors: Lutz G. Guertler, Muenchen (DE); Josef Eberle, Freising (DE); Albrecht v. Brunn, Augsburg (DE); Stefan Knapp, Marburg-Wehrshausen (DE); Hans-Peter Hauser, Marburg (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/886,149

(22) Filed: Jun. 22, 2001

(65) Prior Publication Data

US 2003/0003442 A1 Jan. 2, 2003

Related U.S. Application Data

(60) Continuation of application No. 09/109,916, filed on Jul. 2, 1998, now Pat. No. 6,277,561, which is a division of application No. 08/468,059, filed on Jun. 6, 1995, now Pat. No. 5,840,480, which is a division of application No. 08/132,653, filed on Oct. 5, 1993, now abandoned.

(30) Foreign Application Priority Data

| | | |
|---|---|---|
| Oct. 6, 1992 | (DE) | 42 33 646 |
| Oct. 22, 1992 | (DE) | 43 35 718 |
| Dec. 30, 1992 | (DE) | 42 44 541 |
| Jun. 1, 1993 | (DE) | 43 18 186 |

(51) Int. Cl.[7] .......... A61K 21/04; C07H 21/04
(52) U.S. Cl. .......... 424/208.1; 536/23.72
(58) Field of Search .......... 536/23.72; 424/208.1

(56) References Cited

U.S. PATENT DOCUMENTS 5,304,466 A 4/1994 De Leys et qal. .............. 435/5

OTHER PUBLICATIONS

De Leys et al., *J. Virol.* 64:1207–1216 (1990).

Gürtlrt, et al., *J. Virol.* 68:1581–1585 (1994).

Vanden Hgesevelde et al., "Genomic Cloning and Complete Sequence Analysis of a Highly Devergent African Human Immunodeficiency Virus Isolate," *J. Virol*, pp. 1586–1596.

Rehle et al., "Int. Conf AIDS (Netherlands)," vol. 8, No. 3, p. 34, ab. P.A. 6138.

Gürtler et al., "Int. Conf. AIDS (Germany)," vol. p, No. 1, p. 159, ab. PO–A10–147, 1993.

De Leys et al., Int. Conf. AIDS (Italy), vol. 7, No. 1, p. 131, ab. M.A. 1157, 1991.

Sharp et al., "Origins and Diversity of Human Immunodeficiency Viruses," AIDS, 8 (Suppl. 1):S27–S42, 1994.

Vanden Hgesevelde et al., "Molecular Cloning and Complete Sequence Analysis of Highly Divergent African HIV Isolate," International Conference AIDS, 1991.

Roitt et al., "Immunology," pp. 61–66, Gower Med. Publishing, 1985.

Fahey & Schooley, Status of Immune–Based Therapies in HIV Infections ans AIDS, Clinical Exp. Immunol., 88, pp. 1–5, 1992.

Fox, "No Winners Against AIDS," Bio/Technology, vol. 12, 1994.

*Primary Examiner*—Hankyel T. Park
(74) *Attorney, Agent, or Firm*—Finnegan, Henderson, Farabow, Garrett & Dunner, LLP

(57) ABSTRACT

A novel immunodeficiency virus is disclosed which has the designation MVP-5180/91 and which has been deposited with the European Collection of Animal Cell Cultures (ECACC) under No. V 920 52 318. The characteristic antigens which can be obtained from it and which can be employed for detecting antibodies against retroviruses which are associated with immunodeficiency diseases are also disclosed, as are the DNA and amino acid sequences of the virus.

48 Claims, 18 Drawing Sheets

SEQUENCE OF MVP-5180

(SEQ. ID NO. 56)

```
   1 CTGGATGGGT TAATTTACTC CCATAAGAGA GCAGAAATCC TGGATCTCTG
  51 GATATATCAC ACTCAGGGAT TCTTCCCTGA TTGGCAGTGT TACACACCGG
 101 GACCAGGACC TAGATTCCCA CTGACATTTG GATGGTTGTT TAAACTGGTA
 151 CCAGTGTCAG CAGAAGAGGC AGAGAGACTG GGTAATACAA ATGAAGATGC
 201 TAGTCTTCTA CATCCAGCTT GTAATCATGG AGCTGAGGAT GCACACGGGG
 251 AGATACTAAA ATGGCAGTTT GATAGATCAT TAGGCTTAAC ACATATAGCC
 301 CTGCAAAAGC ACCCAGAGCT CTTCCCCAAG TAACTGACAC TGCGGGACTT
 351 TCCAGACTGC TGACACTGCG GGGACTTTCC AGCGTGGGAG GGATAAGGGG
 401 CGGTTCGGGG AGTGGCTAAC CCTCAGATGC TGCATATAAG CAGCTGCTTT
 451 CCGCTTGTAC CGGGTCTTAG TTAGAGGACC AGGTCTGAGC CCGGGAGCTC
 501 CCTGGCCTCT AGCTGAACCC GCTGCTTAAC GCTCAATAAA GCTTGCCTTG
 551 AGTGAGAAGC AGTGTGTGCT CATCTGTTCA ACCCTGGTGT CTAGAGATCC
 601 CTCAGATCAC TTAGACTGAA GCAGAAAATC TCTAGCAGTG GCGCCCGAAC
 651 AGGGACGCGA AAGTGAAAGT GGAACCAGGG AAGAAAACCT CCGACGCAAC
 701 GGGCTCGGCT TAGCGGAGTG CACCTGCTAA GAGGCGAGAG GAACTCACAA
 751 GAGGGTGAGT AAATTTGCTG GCGGTGGCCA GACCTAGGGG AAGGGCGAAG
 801 TCCCTAGGGG AGGAAGATGG GTGCGAGAGC GTCTGTGTTG ACAGGGAGTA
 851 AATTGGATGC ATGGGAACGA ATTAGGTTAA GGCCAGGATC TAAAAAGGCA
 901 TATAGGCTAA AACATTTAGT ATGGGCAAGC AGGGAGCTGG AAAGATACGC
 951 ATGTAATCCT GGTCTATTAG AAACTGCAGA AGGTACTGAG CAACTGCTAC
1001 AGCAGTTAGA GCCAGCTCTC AAGACAGGGT CAGAGGACCT GAAATCTCTC
1051 TGGAACGCAA TAGCAGTACT CTGGTGCGTT CACAACAGAT TTGACATCCG
1101 AGATACACAG CAGGCAATAC AAAAGTTAAA GGAAGTAATG GCAAGCAGGA
1151 AGTCTGCAGA GGCCGCTAAG GAAGAAACAA GCCCTAGGCA GACAAGTCAA
1201 AATTACCCTA TAGTAACAAA TGCACAGGGA CAAATGGTAC ATCAAGCCAT
```

FIG. 4-1

1251 CTCCCCCAGG ACTTTAAATG CATGGGTAAA GGCAGTAGAA GAGAAGGCCT
1301 TTAACCCTGA AATTATTCCT ATGTTTATGG CATTATCAGA AGGGGCTGTC
1351 CCCTATGATA TCAATACCAT GCTGAATGCC ATAGGGGGAC ACCAAGGGGC
1401 TTTACAAGTG TTGAAGGAAG TAATCAATGA GGAAGCAGCA GAATGGGATA
1451 GAACTCATCC ACCAGCAATG GGGCCGTTAC CACCAGGGCA GATAAGGGAA
1501 CCAACAGGAA GTGACATTGC TGGAACAACT AGCACACAGC AAGAGCAAAT
1551 TATATGGACT ACTAGAGGGG CTAACTCTAT CCCAGTAGGA GACATCTATA
1601 GAAAATGGAT AGTGCTAGGA CTAAACAAAA TGGTAAAAAT GTACAGTCCA
1651 GTGAGCATCT TAGATATTAG GCAGGGACCA AAAGAACCAT TCAGAGATTA
1701 TGTAGATCGG TTTTACAAAA CATTAAGAGC TGAGCAAGCT ACTCAAGAAG
1751 TAAAGAATTG GATGACAGAA ACCTTGCTTG TTCAGAATTC AAACCCAGAT
1801 TGTAAACAAA TTCTGAAAGC ATTAGGACCA GAAGCTACTT TAGAAGAAAT
1851 GATGGTAGCC TGTCAAGGAG TAGGAGGGCC AACTCACAAG GCAAAAATAC
1901 TAGCAGAAGC AATGGCTTCT GCCCAGCAAG ATTTAAAAGG AGGATACACA
1951 GCAGTATTCA TGCAAAGAGG GCAGAATCCA AATAGAAAAG GGCCCATAAA
2001 ATGCTTCAAT TGTGGAAAAG AGGGACATAT AGCAAAAAAC TGTCGAGCAC
2051 CTAGAAAAAG GGGTTGCTGG AAATGTGGAC AGGAAGGTCA CCAAATGAAA
2101 GATTGCAAAA ATGGAAGACA GGCAAATTTT TTAGGGAAGT ACTGGCCTCC
2151 GGGGGGCACG AGGCCAGGCA ATTATGTGCA GAAACAAGTG TCCCCATCAG
2201 CCCCACCAAT GGAGGAGGCA GTGAAGGAAC AAGAGAATCA GAGTCAGAAG
2251 GGGGATCAGG AAGAGCTGTA CCCATTTGCC TCCCTCAAAT CCCTCTTTGG
2301 GACAGACCAA TAGTCACAGC AAAGGTTGGG GGTCATCTAT GTGAGGCTTT
2351 ACTGGATACA GGGGCAGATG ATACAGTATT AAATAACATA CAATTAGAAG
2401 GAAGATGGAC ACCAAAAATG ATAGGGGGTA TAGGAGGCTT TATAAAAGTA
2451 AAAGAGTATA ACAATGTGAC AGTAGAAGTA CAAGGAAAGG AAGTACAGGG
2501 AACAGTATTG GTGGGACCTA CTCCTGTTAA TATTCTTGGG AGAAACATAT
2551 TGACAGGATT AGGATGTACA CTAAATTTCC CTATAAGTCC CATAGCCCCA

*FIG. 4-2*

2601 GTGCCAGTAA AGCTAAAACC AGGAATGGAT GGACCAAAAG TAAAACAATG
2651 GCCCCTATCT AGAGAGAAAA TAGAAGCACT AACTGCAATA TGTCAAGAAA
2701 TGGAACAGGA AGGAAAAATC TCAAGAATAG GACCTGAAAA TCCTTATAAT
2751 ACACCTATTT TTGCTATAAA AAAGAAAGAT AGCACTAAGT GGAGAAAATT
2801 GGTAGACTTC AGAGAATTAA ATAAAAGAAC ACAAGATTTC TGGGAGGTGC
2851 AATTAGGTAT TCCACATCCA GGGGGTTTAA AGCAAAGGCA ATCTGTTACA
2901 GTCTTAGATG TAGGAGATGC TTATTTCTCA TGCCCTTTAG ATCCAGACTT
2951 TAGAAAATAC ACTGCCTTCA CTATTCCTAG TGTGAACAAT GAGACCCCAG
3001 GAGTAAGATA CCAGTACAAT GTCCTCCCGC AAGGGTGGAA AGGTTCACCA
3051 GCCATATTTC AGAGTTCAAT GACAAAGATT CTAGATCCAT TTAGAAAAAG
3101 CAACCCAGAA GTAGAAATTT ATCAGTACAT AGATGACTTA TATGTAGGAT
3151 CAGATTTACC ATTGGCAGAA CATAGAAAGA GGGTCGAATT GCTTAGGGAA
3201 CATTTATATC AGTGGGGATT TACTACCCCT GATAAAAAGC ATCAGAAGGA
3251 ACCTCCCTTT TTATGGATGG GATATGAGCT CCACCCAGAC AAGTGGACAG
3301 TACAGCCCAT CCAATTGCCT GACAAAGAAG TGTGGACAGT AAATGATATA
3351 CAAAAATTAG TAGGAAAATT AAATTGGGCA AGTCAAATCT ATCAAGGAAT
3401 TAGAGTAAAA GAATTGTGCA AGTTAATCAG AGGAACCAAA TCATTGACAG
3451 AGGTAGTACC TTTAAGTAAA GAGGCAGAAC TAGAATTAGA AGAAAACAGA
3501 GAAAAGCTAA AAGAGCCAGT ACATGGAGTA TATTACCAGC CTGACAAAGA
3551 CTTGTGGGTT AGTATTCAGA AGCATGGAGA AGGGCAATGG ACTTACCAGG
3601 TATATCAGGA TGAACATAAG AACCTTAAAA CAGGAAAATA TGCTAGGCAA
3651 AAGGCCTCCC ACACAAATGA TATAAGACAA TTGGCAGAAG TAGTCCAGAA
3701 GGTGTCTCAA GAAGCTATAG TTATATGGGG GAAATTACCT AAATTCAGGC
3751 TGCCAGTTAC TAGAGAAACT TGGGAAACTT GGTGGGCAGA ATATTGGCAG
3801 GCCACCTGGA TTCCTGAATG GGAATTTGTC AGCACACCCC CATTGATCAA
3851 ATTATGGTAC CAGTTAGAAA CAGAACCTAT TGTAGGGGCA GAAACCTTTT
3901 ATGTAGATGG AGCAGCTAAT AGGAATACAA AACTAGGAAA GGCGGGATAT

*FIG. 4-3*

```
3951 GTTACAGAAC AAGGAAAACA GAACATAATA AAGTTAGAAG AGACAACCAA
4001 TCAAAAGGCT GAATTAATGG CTGTATTAAT AGCCTTGCAG GATTCCAAGG
4051 AGCAAGTAAA CATAGTAACA GACTCACAAT ATGTATTGGG CATCATATCC
4101 TCCCAACCAA CACAGAGTGA CTCCCCTATA GTTCAGCAGA TAATAGAGGA
4151 ACTAACAAAA AAGGAACGAG TGTATCTTAC ATGGGTTCCT GCTCACAAAG
4201 GCATAGGAGG AAATGAAAAA ATAGATAAAT TAGTAAGCAA AGACATTAGA
4251 AGAGTCCTGT TCCTGGAAGG AATAGATCAG GCACAAGAAG ATCATGAAAA
4301 ATATCATAGT AATTGGAGAG CATTAGCTAG TGACTTTGGA TTACCACCAA
4351 TAGTAGCCAA GGAAATCATT GCTAGTTGTC CTAAATGCCA TATAAAAGGG
4401 GAAGCAACGC ATGGTCAAGT AGACTACAGC CCAGAGATAT GGCAAATGGA
4451 TTGTACACAT TTAGAAGGCA AAATCATAAT AGTTGCTGTC CATGTAGCAA
4501 GTGACTTTAT AGAAGCAGAG GTGATACCAG CAGAAACAGG ACAGGAAACT
4551 GCCTATTTCC TGTTAAAATT AGCAGCAAGA TGGCCTGTCA AAGTAATACA
4601 TACAGACAAT GGACCTAATT TTACAAGTGC AGCCATGAAA GCTGCATGTT
4651 GGTGGACAGG CATACAACAT GAGTTTGGGA TACCATATAA TCCACAAAGT
4701 CAAGGAGTAG TAGAAGCCAT GAATAAAGAA TTAAAATCTA TTATACAGCA
4751 GGTGAGGGAC CAAGCAGAGC ATTTAAAAAC AGCAGTACAA ATGGCAGTCT
4801 TTGTTCACAA TTTTAAAAGA AAAGGGGGGA TTGGGGGGTA CACTGCAGGG
4851 GAGAGACTAA TAGACATACT AGCATCACAA ATACAAACAA CAGAACTACA
4901 AAAACAAATT TTAAAAATCA ACAATTTTCG GGTCTATTAC AGAGATAGCA
4951 GAGACCCTAT TTGGAAAGGA CCGGCACAAC TCCTGTGGAA AGGTGAGGGG
5001 GCAGTAGTCA TACAAGATAA AGGAGACATT AAAGTGGTAC CAAGAAGAAA
5051 GGCAAAAATA ATCAGAGATT ATGGAAAACA GATGGCAGGT ACTGATAGTA
5101 TGGCAAATAG ACAGACAGAA AGTGAAAGCA TGGAACAGCC TGGTGAAATA
5151 CCATAAATAC ATGTCTAAGA AGGCCGCGAA CTGGCGTTAT AGGCATCATT
5201 ATGAATCCAG GAATCCAAAA GTCAGTTCGG CGGTGTATAT TCCAGTAGCA
5251 GAAGCTGATA TAGTGGTCAC CACATATTGG GGATTAATGC CAGGGGAAAG
```

FIG. 4-4

5301 AGAGGAACAC TTGGGACATG GGGTTAGTAT AGAATGGCAA TACAAGGAGT
5351 ATAAAACACA GATTGATCCT GAAACAGCAG ACAGGATGAT ACATCTGCAT
5401 TATTTCACAT GTTTTACAGA ATCAGCAATC AGGAAGGCCA TTCTAGGGCA
5451 GAGAGTGCTG ACCAAGTGTG AATACCTGGC AGGACATAGT CAGGTAGGGA
5501 CACTACAATT CTTAGCCTTG AAAGCAGTAG TGAAAGTAAA AAGAAATAAG
5551 CCTCCCCTAC CCAGTGTCCA GAGATTAACA GAAGATAGAT GGAACAAGCC
5601 CTGGAAAATC AGGGACCAGC TAGGGAGCCA TTCAATGAAT GGACACTAGA
5651 GCTCCTGGAA GAGCTGAAAG AAGAAGCAGT AAGACATTTC CCTAGGCCTT
5701 GGTTACAAGC CTGTGGGCAG TACATTTATG AGACTTATGG AGACACTTGG
5751 GAAGGAGTTA TGGCAATTAT AAGAATCTTA CAACAACTAC TGTTTACCCA
5801 TTATAGAATT GGATGCCAAC ATAGTAGAAT AGGAATTCTC CCATCTAACA
5851 CAAGAGGAAG AGGAAGAAGA AATGGATCCA GTAGATCCTG AGATGCCCCC
5901 TTGGCATCAC CCTGGGAGCA AGCCCCAAAC CCCTTGTAAT AATTGCTATT
5951 GCAAAAGATG CTGCTATCAT TGCTATGTTT GTTTCACAAA GAAGGGTTTG
6001 GGAATCTCCC ATGGCAGGAA GAAGCGAAGA AGACCAGCAG CTGCTGCAAG
6051 CTATCCAGAT AATAAAGATC CTGTACCAGA GCAGTAAGTA ACGCTGATGC
6101 ATCAAGAGAA CCTGCTAGCC TTAATAGCTT TAAGTGCTTT GTGTCTTATA
6151 AATGTACTTA TATGGTTGTT TAACCTTAGA ATTTATTTAG TGCAAAGAAA
6201 ACAAGATAGA AGGGAGCAGG AAATACTTGA AAGATTAAGG AGAATAAAGG
6251 AAATCAGGGA TGACAGTGAC TATGAAAGTA ATGAAGAAGA ACAACAGGAA
6301 GTCATGGAGC TTATACATAG CCATGGCTTT GCTAATCCCA TGTTTGAGTT
6351 ATAGTAAACA ATTGTATGCC ACAGTTTATT CTGGGGTACC TGTATGGGAA
6401 GAGGCAGCAC CAGTACTATT CTGTGCTTCA GATGCTAACC TAACAAGCAC
6451 TGAACAGCAT AATATTTGGG CATCACAAGC CTGCGTTCCT ACAGATCCCA
6501 ATCCACATGA ATTTCCACTA GGCAATGTGA CAGATAACTT TGATATATGG
6551 AAAAATTACA TGGTGGACCA AATGCATGAA GACATCATTA GTTTGTGGGA
6601 ACAGAGTTTA AAGCCTTGTG AGAAAATGAC TTTCTTATGT GTACAAATGA

*FIG. 4-5*

6651 ACTGTGTAGA TCTGCAAACA AATAAAACAG GCCTATTAAA TGAGACAATA
6701 AATGAGATGA GAAATTGTAG TTTTAATGTA ACTACAGTCC TCACAGACAA
6751 AAAGGAGCAA AAACAGGCTC TATTCTATGT ATCAGATCTG AGTAAGGTTA
6801 ATGACTCAAA TGCAGTAAAT GGAACAACAT ATATGTTAAC TAATTGTAAC
6851 TCCACAATTA TCAAGCAGGC CTGTCCGAAG GTAAGTTTTG AGCCCATTCC
6901 CATACACTAT TGTGCTCCAA CAGGATATGC CATCTTTAAG TGTAATGACA
6951 CAGACTTTAA TGGAACAGGC CTATGCCACA ATATTTCAGT GGTTACTTGT
7001 ACACATGGCA TCAAGCCAAC AGTAAGTACT CAACTAATAC TGAATGGGAC
7051 ACTCTCTAGA GAAAAGATAA GAATTATGGG AAAAAATATT ACAGAATCAG
7101 CAAAGAATAT CATAGTAACC CTAAACACTC CTATAAACAT GACCTGCATA
7151 AGAGAAGGAA TTGCAGAGGT ACAAGATATA TATACAGGTC CAATGAGATG
7201 GCGCAGTATG ACACTTAAAA GAAGTAACAA TACATCACCA AGATCAAGGG
7251 TAGCTTATTG TACATATAAT AAGACTGTAT GGGAAAATGC CCTACAACAA
7301 ACAGCTATAA GGTATTTAAA TCTTGTAAAC CAAACAGAGA ATGTTACCAT
7351 AATATTCAGC AGAACTAGTG GTGGAGATGC AGAAGTAAGC CATTTACATT
7401 TTAACTGTCA TGGAGAATTC TTTTATTGTA ACACATCTGG GATGTTTAAC
7451 TATACTTTTA TCAACTGTAC AAAGTCCGGA TGCCAGGAGA TCAAAGGGAG
7501 CAATGAGACC AATAAAAATG GTACTATACC TTGCAAGTTA AGACAGCTAG
7551 TAAGATCATG GATGAAGGGA GAGTCGAGAA TCTATGCACC TCCCATCCCC
7601 GGCAACTTAA CATGTCATTC CAACATAACT GGAATGATTC TACAGTTAGA
7651 TCAACCATGG AATTCCACAG GTGAAAATAC ACTTAGACCA GTAGGGGGAG
7701 ATATGAAAGA TATATGGAGA ACTAAATTGT ACAACTACAA AGTAGTACAG
7751 ATAAAACCTT TTAGTGTAGC ACCTACAAAA ATGTCAAGAC CAATAATAAA
7801 CATTCACACC CCTCACAGGG AAAAAAGAGC AGTAGGATTG GGAATGCTAT
7851 TCTTGGGGGT GCTAAGTGCA GCAGGTAGCA CTATGGGCGC AGCGGCAACA
7901 GCGCTGACGG TACGGACCCA CAGTGTACTG AAGGGTATAG TGCAACAGCA
7951 GGACAACCTG CTGAGAGCGA TACAGGCCCA GCAACACTTG CTGAGGTTAT

FIG. 4-6

8001 CTGTATGGGG TATTAGACAA CTCCGAGCTC GCCTGCAAGC CTTAGAAACC

8051 CTTATACAGA ATCAGCAACG CCTAAACCTA TGGGGCTGTA AAGGAAAACT

8101 AATCTGTTAC ACATCAGTAA AATGGAACAC ATCATGGTCA GGAAGATATA

8151 ATGATGACAG TATTTGGGAC AACCTTACAT GGCAGCAATG GGACCAACAC

8201 ATAAACAATG TAAGCTCCAT TATATATGAT GAAATACAAG CAGCACAAGA

8251 CCAACAGGAA AAGAATGTAA AAGCATTGTT GGAGCTAGAT GAATGGGCCT

8301 CTCTTTGGAA TTGGTTTGAC ATAACTAAAT GGTTGTGGTA TATAAAAATA

8351 GCTATAATCA TAGTGGGAGC ACTAATAGGT ATAAGAGTTA TTATGATAAT

8401 ACTTAATCTA GTGAAGAACA TTAGGCAGGG ATATCAACCC CTCTCGTTGC

8451 AGATCCCTGT CCCACACCGG CAGGAAGCAG AAACGCCAGG AAGAACAGGA

8501 GAAGAAGGTG GAGAAGGAGA CAGGCCCAAG TGGACAGCCT TGCCACCAGG

8551 ATTCTTGCAA CAGTTGTACA CGGATCTCAG GACAATAATC TTGTGGACTT

8601 ACCACCTCTT GAGCAACTTA ATATCAGGGA TCCGGAGGCT GATCGACTAC

8651 CTGGGACTGG GACTGTGGAT CCTGGGACAA AAGACAATTG AAGCTTGTAG

8701 ACTTTGTGGA GCTGTAATGC AATATTGGCT ACAAGAATTG AAAAATAGTG

8751 CTACAAACCT GCTTGATACT ATTGCAGTGT CAGTTGCCAA TTGGACTGAC

8801 GGCATCATCT TAGGTCTACA AAGAATAGGA CAAGGATTCC TTCACATCCC

8851 AAGAAGAATT AGACAAGGTG CAGAAAGAAT CTTAGTGTAA CATGGGGAAT

8901 GCATGGAGCA AAAGCAAATT TGCAGGATGG TCAGAAGTAA GAGATAGAAT

8951 GAGACGATCC TCCTCTGATC CTCAACAACC ATGTGCACCT GGAGTAGGAG

9001 CTGTCTCCAG GGAGTTAGCA ACTAGAGGGG GAATATCAAG TTCCCACACT

9051 CCTCAAAACA ATGCAGCCCT TGCATTCCTA GACAGCCACA AAGATGAGGA

9101 TGTAGGCTTC CCAGTAAGAC CTCAAGTGCC TCTAAGGCCA ATGACCTTTA

9151 AAGCAGCCTT TGACCTCAGC TTCTTTTTAA AAGAAAAGGG AGGACTGGAT

9201 GGGTTAATTT ACTCCCATAA GAGAGCAGAA ATCCTGGATC TCTGGATATA

9251 TCACACTCAG GGATTCTTCC CTGATTGGCA GTGTTACACA CCGGGACCAG

9301 GACCTAGATT CCCACTGACA TTTGGATGGT TGTTTAAACT GGTACCAGTG

*FIG. 4-7*

9351 TCAGCAGAAG AGGCAGAGAG ACTGGGTAAT ACAAATGAAG ATGCTAGTCT
9401 TCTACATCCA GCTTGTAATC ATGGAGCTGA GGATGCACAC GGGGAGATAC
9451 TAAAATGGCA GTTTGATAGA TCATTAGGCT TAACACATAT AGCCCTGCAA
9501 AAGCACCCAG AGCTCTTCCC CAAGTAACTG ACACTGCGGG ACTTTCCAGA
9551 CTGCTGACAC TGCGGGGACT TTCCAGCGTG GGAGGGATAA GGGGCGGTTC
9601 GGGGAGTGGC TAACCCTCAG ATGCTGCATA TAAGCAGCTG CTTTCCGCTT
9651 GTACCGGGTC TTAGTTAGAG GACCAGGTCT GAGCCCGGGA GCTCCCTGGC
9701 CTCTAGCTGA ACCCGCTGCT TAACGCTCAA TAAAGCTTGC CTTGAGTGAG
9751 AAGCAGTGTG TGCTCATCTG TTCAACCCTG GTGTCTAGAG ATC

FIG. 4-8

(SEQUENCE ID NO. 57 + 58)

```
MvP5180
 685 AAACCTCCGACGCAACGGGCTCGGCTTAGCGGAGTGCACCTGCTAAGAGG  734
     |||||||| |||||||||||||||||||||||||||||||||||||||||
   1 aaacctccaacgcaacgggctcggcttagcggagtgcacctgctaagagg  50

 735 CGAGAGGAACTCACAAGAGGGTGAGTAAATTTGCTGGCGGTGGCCAGACC  784
     ||||||||||||||||||||||||||||||||||||||||||||||||||
  51 cgagaggaactcacaagagggtgagtaaatttgctggcggtggccagacc  100

 785 TAGGGGAAGGGCGAAGTCCCTAGGGGAGGAAGATGGGTGCGAGAGCGTCT  834
     ||||||||||||||||||||||||||||||||||||||||||||  ||||
 101 taggggaagggcgaagtccctaggggaggaagatgggtgcgagacggtct  150

 835 GTGTTGACAGGGAGTAAATTGGATGCATGGGAACGAATTAGGTTAAGGCC  884
     ||||||||||||||||||||||||||||||||||||||||||||||||||
 151 gtgttgacagggagtaaattggatgcatgggaacgaattaggttaaggcc  200

 885 AGGATCTAAAAAGGCATATAGGCTAAAACATTTAGTATGGGCAAGCAGGG  934
     ||||||||||||||||||||||||||||||||||||||||||||||||||
 201 aggatctaaaaaggcatataggctaaaAcatttagtatgggcaagcaggg  200

 935 AGCTGGAAAGATACGCATGTAATCCTGGTCTATTAGAAACTGCAGAAGGT  984
     |||||||||||||||||| ||||||||||||| |||||||||||||||||
 251 agctggaaagatacgcatataatcctggtctactagaaactgcagaaggt  300

 985 ACTGAGCAACTGCTACAGCAGTTAGAGCCAGCTCTCAAGACAGGGTCAGA  1034
     ||||| ||||||||||||||||||||||||||||||||||||||||||||
 301 actgaacaactgctacagcagttagagccagctctcaagacagggtcaga  350

1035 GGACCTGAAATCTCTCTGGAACGCAATAGCAGTACTCTGGTGCGTTCACA  1084
     |||||||||||| |||||||||||||||||||||||||||||||||||||
 351 ggacctgaaatccctctggaacgcaatagcagtactctggtgcgttcaca  400

1085 ACAGATTTGACATCCGAGATACACAGCAGGCAATACAAAAGTTAAAGGAA  1134
     ||||||||||||||||||||||||||||||||||||||||||||||||||
 401 acagatttgacatccgagatacacagcaggcaatacaaaagttaaaggaa  450

1135 GTAATGGCAAGCAGGAAGTCTGCAGAGGCCGCTAAGGAAGAAACAAGCCC  1184
     |||||||||||||||||||||||||||||||||||||||||||||||| |
 451 gtaatggcaagcaggaagtctgcagaggccgctaaggaagaaacaagctc  500
```

FIG. 6-1

```
                  .         .         .         .         .
1185  TAGGCAGACAAGTCAAAATTACCCTATAGTAACAAATGCACAGGGACAAA  1234
       ||||| |||||||||||||||||||||||||||||||||||||||||||
 501  aaggcaggcaagtcaaaattaccctatagtaacaaatgcacagggacaaa  550

                  .         .         .         .         .
1235  TGGTACATCAAGCCATCTCCCCCAGGACTTTAAATGCATGGGTAAAGGCA  1284
      |||||||||||||||| ||||| |||||||||||||||||||||||||||
 551  tggtacatcaagccatatcccctaggactttaaatgcatgggtaaaggca  600

                  .         .         .         .         .
1285  GTAGAAGAGAAGGCCTTTAACCCTGAAATTATTCCTATGTTTATGGCATT  1334
      |||||||| |||||||||||||||||||||||||||||||||||||||||
 601  gtagaagaaaaggcctttaaccctgaaattattcctatgtttatggcatt  650

                  .         .         .         .         .
1335  ATCAGAAGGGGCTGTCCCCTATGATATCAATACCATGCTGAATGCCATAG  1384
      ||||||||||||||||||||||||||||||||||||||||||||||||||
 651  atcagaaggggctgtcccctatgatatcaataccatgctgaatgccatag  700

                  .         .         .         .         .
1385  GGGGACACCAAGGGGCTTTACAAGTGTTGAAGGAAGTAATCAATGAGGAA  1434
      ||||||||||||||||||||||||||||||||||||||||||||||||||
 701  ggggacaccaaggggctttacaagtgttgaaggaagtaatcaatgaggaa  750

                  .         .         .         .         .
1435  GCAGCAGAATGGGATAGAACTCATCCACCAGCAATGGGGCCGTTACCACC  1484
      |||||||| |||||||||||||||||||||||||||||||||||||||||
 751  gcagcagattgggatagaactcatccaccagcaatggggccgttaccacc  800

                  .         .         .         .         .
1485  AGGGCAGATAAGGGAACCAACAGGAAGTGACATTGCTGGAACAACTAGCA  1534
      ||||||||||||||||||||||||||||||||||||||||||||||||||
 801  agggcagataagggaaccaacaggaagtgacattgctggaacaactagca  850

                  .         .         .         .         .
1535  CACAGCAAGAGCAAATTATATGGACTACTAGAGGGGCTAACTCTATCCCA  1584
      ||||||||||||||||||||||||||||||||||||||||||||||||||
 851  cacagcaagagcaaattatatggactactagaggggctaactctatccca  900

                  .         .         .         .         .
1585  GTAGGAGACATCTATAGAAAATGGATAGTGCTAGGACTAAACAAAATGGT  1634
      |||||||||||||||||||||||||||||| |||||||||||||||||||
 901  gtaggagacatctatagaaaatggatagtgttaggactaaacaaaatggt  950

                  .         .         .         .         .
1635  AAAAATGTACAGTCCAGTGAGCATCTTAGATATTAGGCAGGGACCAAAAG  1684
      ||||||||||||||||||||||||||||||||||||||||||||||||||
 951  aaaaatgtacagtccagtgagcatcttagatattaggcagggaccaaaag  1000
```

*FIG. 6-2*

```
1685  AACCATTCAGAGATTATGTAGATCGGTTTTACAAAACATTAAGAGCTGAG  1734
      ||||||||||||||||||||||||||||||||||||||||||||||||||
1001  aaccattcagagattatgtagatcggttttacaaaacattaagagctgag  1050

1735  CAAGCTACTCAAGAAGTAAAGAATTGGATGACAGAAACCTTGCTTGTTCA  1784
      ||||||||||||||||||||||||||||||||||||||||| ||||||||
1051  caagctactcaagaagtaaagaattggatgacagaaaccctcgttgttca  1100

1785  GAATTCAAACCCAGATTGTAAACAAATTCTGAAAGCATTAGGACCAGAAG  1834
      |||||||||||||||||||||||||||||||||||||||||||||||| |
1101  gaattcaaacccagattgtaaacaaattctgaaagcattaggaccaggag  1150

1835  CTACTTTAGAAGAAATGATGGTAGCCTGTCAAGGAGTAGGAGGGCCAACT  1884
      ||||||||||||||||||||||||||||||||||||||||||||||||||
1151  ctactttagaagaaatgatggtagcctgtcaaggagtaggagggccaact  1200

1885  CACAAGGCAAAAATACTAGCAGAAGCAATGGCTTCTGCCCAGCAAGATTT  1934
      ||||||||||||||||||||||||||||||||||||||||||||||||||
1201  cacaaggcaaaaatactagcagaagcaatggcttctgcccagcaagattt  1250

1935  AAAAGGAGGATACACAGCAGTATTCATGCAAAGAGGGCAGAATCCAAATA  1984
      ||| ||||||||||||||||||||||||||||||||||||||||||||||
1251  aaagggaggatacacagcagtattcatgcaaagagggcagaatccaaata  1300

1985  GAAAAGGGCCCATAAAATGCTTCAATTGTGGAAAAGAGGGACATATAGCA  2034
      |||||||||| |||||||| ||||||||||||||||||||||||||||||
1301  gaaaagggcctataaaatgtttcaattgtggaaaagagggacatatagca  1350

2035  AAAAACTGTCGAGCACCTAGAAAAAGGGGTTGCTGGAAATGTGGACAGGA  2084
      |||||||||||||||||||||| |||||| ||||||||||||||||||||
1351  aaaaactgtcgagcacctagaagaaggggttactggaaatgtggacagga  1400

2085  AGGTCACCAAATGAAAGATTGCAAAAATGGAAGACAGGCAAATTTTTTAG  2134
      ||||||||||||||||||||||||||||||||||||||| ||||||||||
1401  aggtcaccaaatgaaagattgcaaaaatggaagacaggctaattttttag  1450

2135  GGAAGTACTGGCCTCCGGGGGGCACGAGGCCAGGCAATTATGTGCAGAAA  2184
      ||||||||||||||||||||||||||||||||||| ||||||||||||||
1451  ggaagtactggcctccggggggcacgaggccagccaattatgtgcagaaa  1500
```

FIG. 6-3

```
2185 CAAGTGTCCCCATCAGCCCCACCAATGGAGGAGGCAGTGAAGGAACAAGA 2234
     ||||||||||||||||||||||||||||||||||||||||||||||||||
1501 caagtgtccccatcagccccaccaatggaggaggcagtgaaggaacaaga 1550

2235 GAATCAGAGTCAGAAGGGGGATCAGGAAGAGCTGTACCCATTTGCCTCCC 2284
     |||||||| ||| |||||||||||||||||||||||||||||||||||||
1551 gaatcagaatcaaaagggggatcaggaagagctgtacccatttgcctccc 1600

2285 TCAAATCCCTCTTTGGGACAGACCAATAGTCACAGCAAAGGTTGGGGGTC 2334
     ||||||||||||||||||||||||||||||||||||||||||||||| |
1601 tcaaatccctctttgggacagaccaatagtcacagcaaaggttgggggcc 1650

2335 ATCTATGTGAGGCTTTACTGGATACAGGGGCAGATGATACAGTATTAAAT 2384
     ||||||||||||||||||||||||||||||||||||||||||||||||||
1651 atctatgtgaggctttactggatacaggggcagatgatacagtattaaat 1700

2385 AACATACAATTAGAAGGAAGATGGACACCAAAA 2417 (SEQ ID NO:57)
     |||||||||||||||||||||||||||| |||
1701 aacatacaattagaaggaagatggacacccaaa 1733 (SEQ ID NO:58)
```

FIG. 6-4

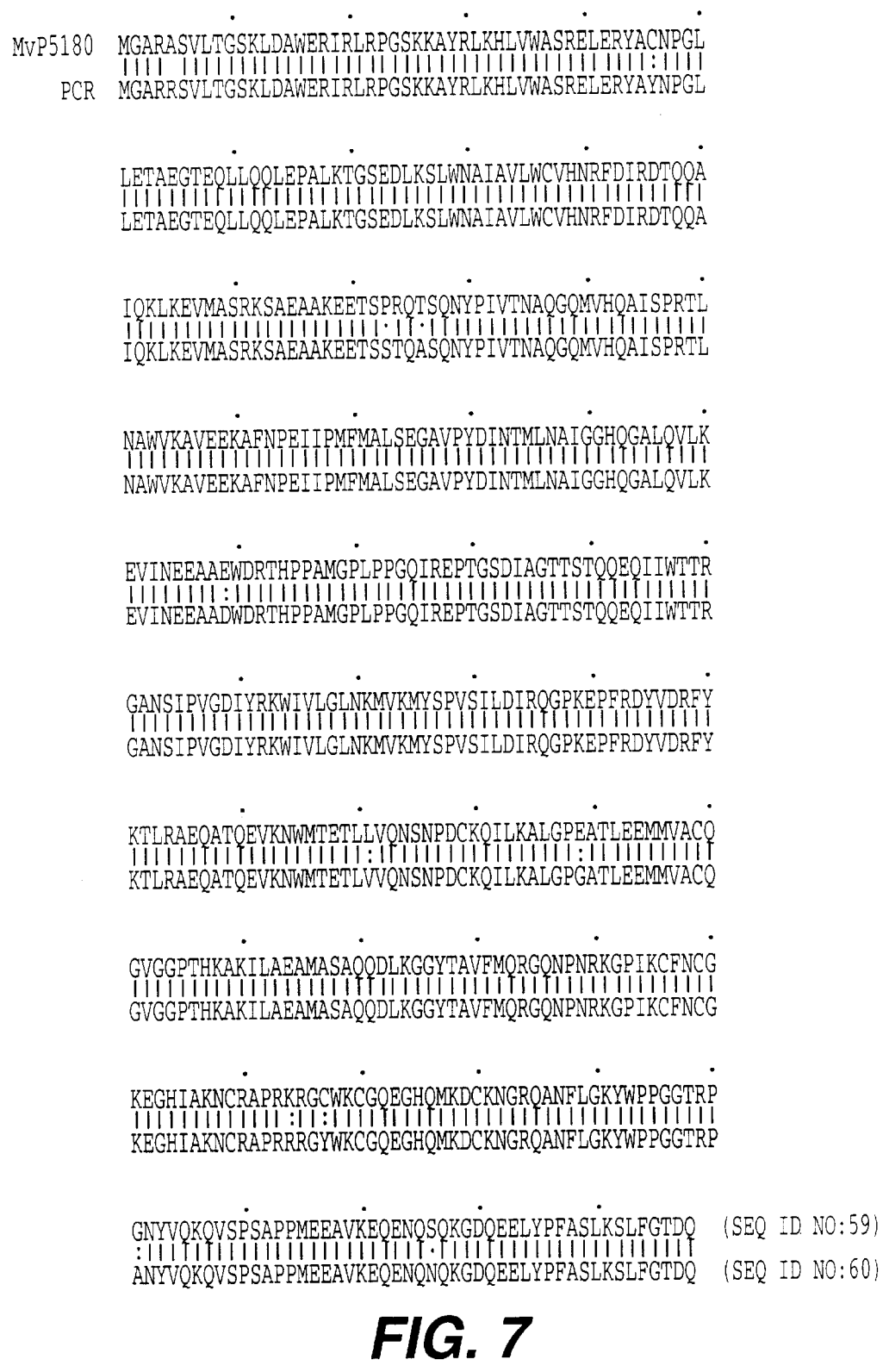

```
MvP5180  MGARASVLTGSKLDAWERIRLRPGSKKAYRLKHLVWASRELERYACNPGL
         |||| ||||||||||||||||||||||||||||||||||||||||:||||
    PCR  MGARRSVLTGSKLDAWERIRLRPGSKKAYRLKHLVWASRELERYAYNPGL

         LETAEGTEQLLQQLEPALKTGSEDLKSLWNAIAVLWCVHNRFDIRDTQQA
         ||||||||||||||||||||||||||||||||||||||||||||||||||
         LETAEGTEQLLQQLEPALKTGSEDLKSLWNAIAVLWCVHNRFDIRDTQQA

         IQKLKEVMASRKSAEAAKEETSPRQTSQNYPIVTNAQGQMVHQAISPRTL
         ||||||||||||||||||||||· |·||||||||||||||||||||||||
         IQKLKEVMASRKSAEAAKEETSSTQASQNYPIVTNAQGQMVHQAISPRTL

         NAWVKAVEEKAFNPEIIPMFMALSEGAVPYDINTMLNAIGGHQGALQVLK
         ||||||||||||||||||||||||||||||||||||||||||||||||||
         NAWVKAVEEKAFNPEIIPMFMALSEGAVPYDINTMLNAIGGHQGALQVLK

         EVINEEAAEWDRTHPPAMGPLPPGQIREPTGSDIAGTTSTQQEQIIWTTR
         ||||||||:|||||||||||||||||||||||||||||||||||||||||
         EVINEEAADWDRTHPPAMGPLPPGQIREPTGSDIAGTTSTQQEQIIWTTR

         GANSIPVGDIYRKWIVLGLNKMVKMYSPVSILDIRQGPKEPFRDYVDRFY
         ||||||||||||||||||||||||||||||||||||||||||||||||||
         GANSIPVGDIYRKWIVLGLNKMVKMYSPVSILDIRQGPKEPFRDYVDRFY

         KTLRAEQATQEVKNWMTETLLVQNSNPDCKQILKALGPEATLEEMMVACQ
         ||||||||||||||||||||:|||||||||||||||||:|||||||||||
         KTLRAEQATQEVKNWMTETLVVQNSNPDCKQILKALGPGATLEEMMVACQ

         GVGGPTHKAKILAEAMASAQQDLKGGYTAVFMQRGQNPNRKGPIKCFNCG
         ||||||||||||||||||||||||||||||||||||||||||||||||||
         GVGGPTHKAKILAEAMASAQQDLKGGYTAVFMQRGQNPNRKGPIKCFNCG

         KEGHIAKNCRAPRKRGCWKCGQEGHQMKDCKNGRQANFLGKYWPPGGTRP
         |||||||||||||:||:|||||||||||||||||||||||||||||||||
         KEGHIAKNCRAPRRRGYWKCGQEGHQMKDCKNGRQANFLGKYWPPGGTRP

         GNYVQKQVSPSAPPMEEAVKEQENQSQKGDQEELYPFASLKSLFGTDQ  (SEQ ID NO:59)
         :||||||||||||||||||||||||·||||||||||||||||||||||
         ANYVQKQVSPSAPPMEEAVKEQENQNQKGDQEELYPFASLKSLFGTDQ  (SEQ ID NO:60)
```

FIG. 7

HIV - 1 (LAI)
(SEQ ID NO:66)

HIV - 5180
(SEQ ID NO:54)

HIV - 2 (ROD)
(SEQ ID NO:67)

RETROVIRUS FROM THE HIV GROUP AND ITS USE

This application is a continuation of U.S. application Ser. No. 09/109,196, filed Jul. 2, 1998, now U.S. Pat. No. 6,277,561, issued Aug. 21, 2001, which is a divisional application of U.S. application Ser. No. 08/468,059, filed Jun. 6, 1995, now U.S. Pat. No. 5,840,480, issued Nov. 24, 1998; which is a divisional application of U.S. application Ser. No. 08/132,653, filed Oct. 5, 1993, now abandoned; the disclosures of all of which are incorporated herein by reference.

The present invention relates to a novel retrovirus from the HIV group, as well as to variants or parts thereof which contain the essential properties of the virus. A process is described for culturing the retrovirus. The invention furthermore relates to the isolation of this retrovirus and to use of the virus, its parts or extracts for medicinal purposes, for diagnostics and in the preparation of vaccines.

Retroviruses which belong to the so-called HIV group lead in humans who are infected by them to disease manifestations which are summarized under the collective term immunodeficiency or AIDS (acquired immune deficiency syndrome).

Epidemiological studies verify that the human immunodeficiency virus (HIV) represents the etiological agent in the vast majority of AIDS (acquired immune deficiency syndrome) cases. A retrovirus which was isolated from a patient and characterized in 1983 received the designation HIV-1 (Barré-Sinoussi, F. et al., Science 220, 868–871 [1983]). A variant of HIV-1 is described in WO 86/02383.

A second group of human immunodeficiency viruses was identified in 1985 in West Africa (Clavel, F. et al., Science 233, 343–346 [1986]) and designated human immunodeficiency virus type 2 (HIV-2) (EP-A-0 239 425). While HIV-2 retroviruses clearly differ from HIV-1, they do exhibit affinity with simian immunodeficiency viruses (SIV-2). Like HIV-1, HIV-2 also leads to AIDS symptomatology.

A further variant of an immunodeficiency retrovirus is described in EP-A-0 345 375 and designated there as HIV-3 retrovirus (ANT 70).

The isolation of a further, variant, immunodeficiency virus is also described in Lancet Vol. 340, September 1992, pp. 681–682.

It is characteristic of human immunodeficiency viruses that they exhibit a high degree of variability, which significantly complicates the comparability of the different isolates. For example, when diverse HIV-1 isolates are compared, high degrees of variability are found in some regions of the genome while other regions are comparatively well conserved (Benn, S. et al., Science 230, 949–951 (1985]). It was also possible to observe an appreciably greater degree of polymorphism in the case of HIV-2 (Clavel, F. et al., Nature 324, 691–695 [1986]). The greatest degree of genetic stability is possessed by regions in the gag and pol genes which encode proteins which are essential for structural and enzymic purposes; some regions in the env gene, and the genes (vif, vpr, tat, rev and nef) encoding regulatory proteins, exhibit a high degree of variability. In addition to this, it was possible to demonstrate that antisera against HIV-1 also crossreact with gag and pol gene products from HIV-2 even though there was only a small degree of sequence homology. Little hybridization of significance likewise took place between these two viruses unless conditions of very low stringency were used (Clavel, F. et al., Nature 324, 691–695 [1986]).

Owing to the wide distribution of retroviruses from the HIV group and to the fact that a period of a few to many years (2–20) exists between the time of infection and the time at which unambiguous symptoms of pathological changes are recognizable, it is of great importance from the epidemiological point of view to determine infection with retroviruses of the HIV group at as early a stage as possible and, above all, in a reliable manner. This is not only of importance when diagnosing patients who exhibit signs of immunodeficiency, but also when monitoring blood donors. It has emerged that, when retroviruses of the HIV-1 or HIV-2 type, or components thereof, are used in detection systems, antibodies can either not be detected or only detected weakly in many sera even though signs of immunodeficiency are present in the patients from which the sera are derived. In certain cases, such detection is possible using the retrovirus from the HIV group according to the invention.

This patent describes the isolation and characterization of a novel human immunodeficiency virus, designated below as MVP-5180/91 (SEQ ID NO:56), which was isolated from the peripheral lymphocytes of a female patient from the Cameroons who was 34 years old in 1991 and who exhibited signs of immunodeficiency. From the point of view of geography, this retrovirus originates from a region in Africa which is located between West Africa, where there is endemic infection with HIV-2 and HIV-1 viruses, and Eastern Central Africa, where it is almost exclusively HIV-1 which is disseminated. Consequently, the present invention relates to a novel retrovirus, designated MVP-5180/91 (SEQ ID NO:56), of the HIV group and its variants, to DNA sequences, amino acid sequences and constituent sequences derived therefrom, and to test kits containing the latter. The retrovirus MVP-5180/91 (SEQ ID NO:56) has been deposited with the European Collection of Animal Cell Cultures (ECACC) PHLS Centre for Applied Microbiology & Research, Porton Down, Salisbury Wilts. SP4 OJG, United Kingdom, on Sep. 23, 1992 under ECACC Accession No. V 920 92 318 in accordance with the stipulations of the Budapest Treaty. The ECACC is located at the PHLS Centre for Applied Microbiology & Research, Porton Down, Salisbury, Wilts, SP4 OJG, U.K. The deposit was made on Sep. 23, 1992, and was assigned Accession No. V 920 92 318. The date of notification of acceptance of the culture was Jan. 21, 1993.

As do HIV-1 and HIV-2, MVP-5180/91 (SEQ ID NO:56) according to the invention grows in the following cell lines: HUT 78, Jurkat cells, C8166 cells and MT-2 cells. The isolation and propagation of viruses is described in detail in the book "Viral Quantitation in HIV Infection, Editor Jean-Marie Andrieu, John Libbey Eurotext, 1991". The procedural methods described in that publication are by reference made a subject of the disclosure of the present application.

In addition to this, the virus according to the invention possesses a reverse transcriptase which is magnesium-dependent but not manganese-dependent. This represents a further property possessed in common with the HIV-1 and HIV-2 viruses.

In order to provide a better understanding of the differences between the MVP-5180/91 (SEQ ID NO:56) virus according to the invention and the HIV-1 and HIV-2 retroviruses, the construction of the retroviruses which cause immunodeficiency will first of all be explained in brief. Within the virus, the RNA is located in a conical core which is assembled from protein subunits which carry the designation p 24 (p for protein). This inner core is surrounded by a protein coat, which is constructed from protein p 17 (outer core), and by a glycoprotein coat which, in addition to lipids, which originate from the host cell, contains the transmembrane protein gp 41 and the coat protein 120 (gp 120). This gp 120 can then bind to the CD-4 receptors of the host cells.

BRIEF DESCRIPTION OF THE DRAWINGS

FIG. 4 depicts the almost complete nucleic acid sequence of the retrovirus MVP-5180/91.

FIG. 6 depicts a comparison of the sequence in FIG. 4 and the sequence obtained using the PCR amplification techniques depicted in FIG. 5.

FIG. 7 depicts a comparison of the amino acid sequences of the GAG protein determined from the sequence of FIG. 4 with the GAG protein sequence obtained using the PCR amplification techniques depicted in FIG. 5.

DETAILED DESCRIPTION OF THE INVENTION

Figure 1:
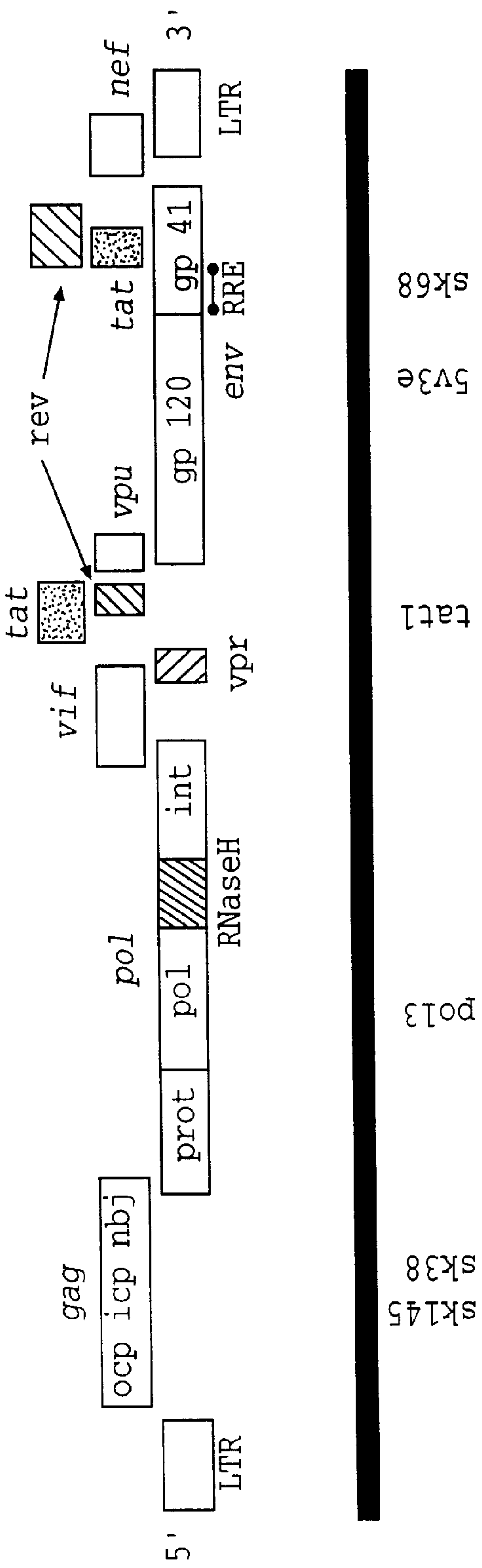
FIG. 1 depicts the arrangement of the genome of retroviruses of the HIV type.

As far as is known, the RNA of HIV viruses—portrayed in a simplified manner—possesses the following gene regions: so-called long terminal repeats (LTR) at each end, together with the following gene regions: gag, pol, env and nef. The gag gene encodes, inter alia, the core proteins, p 24 and p 17, the pol gene encodes, inter alia, the reverse transcriptase, the RNAse H and the integrase, while the env gene encodes the gp 41 and gp 120 glycoproteins of the virus coat. The nef gene encodes a protein having a regulatory function. The arrangement of the genome of retroviruses of the HIV type is shown diagrammatically in FIG. 1.

Figure 2:
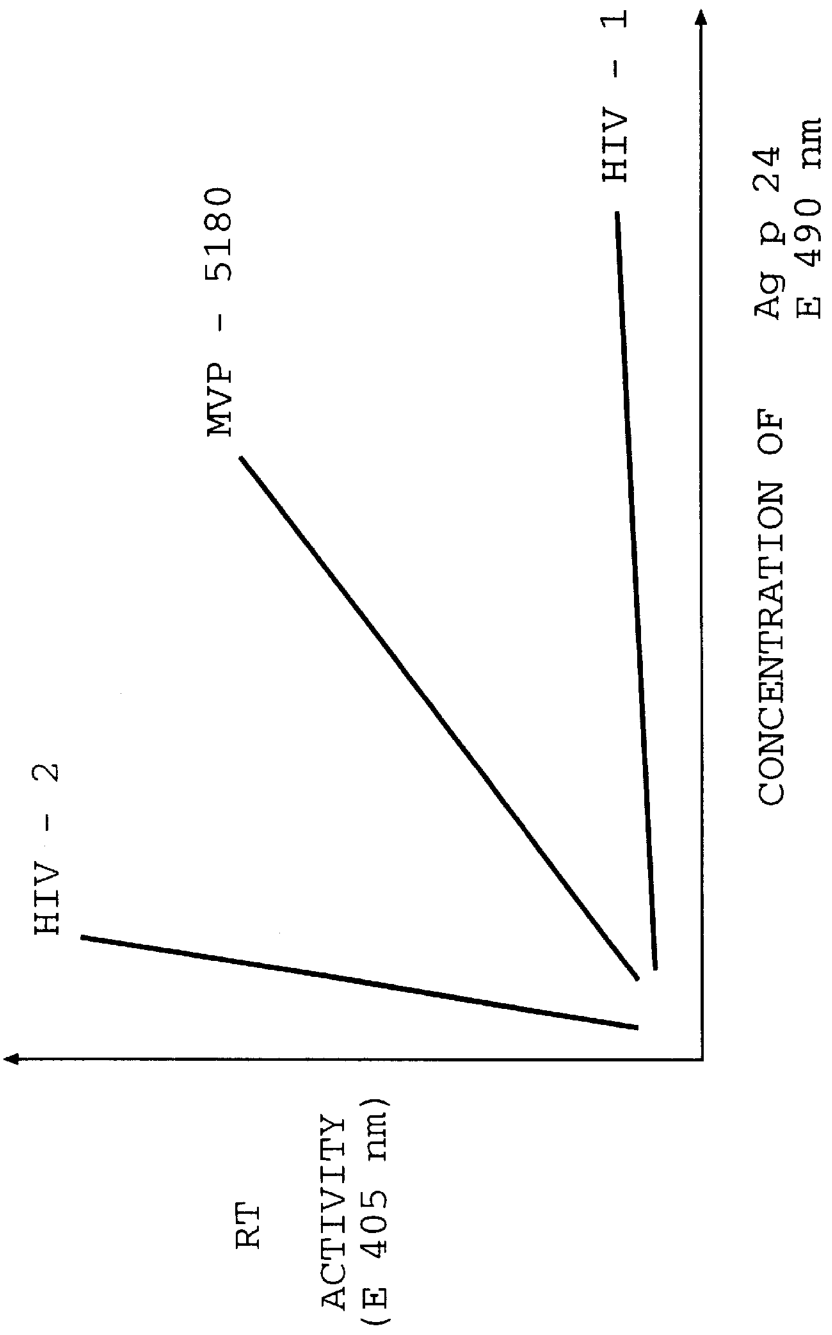
FIG. 2 is a graph depicting the binding affinity for the monoclonal antibody p24 in relation to the content of reverse transcriptase for the retroviruses HIV-1, HIV-2, and MVP-5180/91.

The HIV-1 and HIV-2 retroviruses can be distinguished, inter alia, by testing viral antigen using a monoclonal antibody which is commercially available from Abbott (HIVAG-1 monoclonal) in the form of a test kit and is directed against (HIV-1) p 24. It is known that the content of reverse transcriptase is roughly the same in the HIV-1 and HIV-2 virus types. If, therefore, the extinction (E 490 nm.) obtained in dilutions of the disrupted viruses by means of the antigen-antibody reaction is plotted against the activity of reverse transcriptase, a series of graphs is obtained corresponding roughly to that in FIG. 2. In this context, it is observed that, in the case of HIV-1, the monoclonal antibody employed has a very high binding affinity for p 24 in relation to the content of reverse transcriptase. By contrast, the monoclonal antibody employed has only a very low binding affinity for p 24 in the case of HIV-2, once again in relation to the content of reverse transcriptase. If these measurements are carried out on MVP-5180/91 (SEQ ID NO:56), the curve is then located almost precisely in the centre between the curves for HIV-1 and HIV-2, i.e. the binding affinity of the monoclonal antibody for MVP-5180/91 p 24 is reduced as compared with the case of HIV-1. FIG. 2 shows this relationship diagrammatically, with RT denoting reverse transcriptase, and the protein p 24, against which is directed the monoclonal antibody which is present in the test kit which can be purchased from Abbott, being employed as the antigen (Ag).

The so-called PCR (polymerase chain reaction) system has proved to have a multiplicity of uses in genetic manipulation, and the components which are required for implementing the process can be purchased. Using this process, it is possible to amplify DNA sequences if regions of the sequence to be amplified are known. Short, complementary DNA fragments (oligonucleotides=primers) have then to be synthesized which anneal to a short region of the nucleic acid sequence to be amplified. For carrying out the test, HIV nucleic acids are introduced together with the primers into a reaction mixture which additionally contains a polymerase and nucleotide triphosphates. The polymerization (DNA synthesis) is carried out for a given time and the nucleic acid strands are then separated by heating. After cooling, the polymerization then proceeds once more. If, therefore, the retrovirus according to the invention is an HIV-1 or HIV-2 virus, it should be possible to amplify the nucleic acid using primers which are conserved within the known sequences of the HIV-1 and HIV-2 viruses. Some primers of this type have previously been described (Lauré, F. et al., Lancet ii, (1988) 538–541 for pol 3 and pol 4, and Ou C.Y. et al., Science 239 (1988) 295–297 for sk 38/39 and sk 68/69).

It was discovered that use of particular primer pairs having the following sequence:

gaga (SEQ ID NO:1): CTACT AGTAC CCTTC AGG gagb (SEQ ID NO:2): CGGTC TACAT AGTCT CTAAA G sk38 (SEQ ID NO:3): CCACC TATCC CAGTA GGAGA A sk39 (SEQ ID NO:4): CCTTT GGTCC TTGTC TTATG TCCAG AATGC or po13 (SEQ ID NO:5): TGGGA AGTTC AATTA GGAAT ACCAC po14 (SEQ ID NO:6): CCTAC ATAGA AATCA TCCAT GTATT G po13n (SEQ ID NO:7): TGGAT GTGGG TGATG CATA po14n (SEQ ID NO:8): AGCAC ATTGT ACTGA TATCT A and

SK145 (SEQ ID NO:9): AGTGG GGGGA CATCA AGCAG CC

SK150 (SEQ ID NO:10): TGCTA TGTCA CTTCC CCTTG GT

145-P (SEQ ID NO:11): CCATG CAAAT GTTAA AAGAG AC

150-P (SEQ ID NO:12): GGCCT GGTGC AATAG GCCC or a combination of pol 3 and pol 4 with

UNI-1 (SEQ ID NO:13): GTGCT TCCAC AGGGA TGGAA

UNI-2 (SEQ ID NO:14): ATCAT CCATG TATTG ATA (Donehower L. A. et al. (1990) J. Virol. Methods 28, 33–46) and employing PCR with nested primers, led to weak amplifications of the MVP-5180/91 DNA (SEQ ID NO:56).

No amplification, or only weak amplification as compared with HIV-1, possibly attributable to impurities, was obtained with the following primer sequences:

tat 1 (SEQ ID NO:15): AATGG AGCCA GTAGA TCCTA tat 2 (SEQ ID NO:16): TGTCT CCGCT TCTTC CTGCC tat 1P (SEQ ID NO:17): GAGCC CTGGA AGCAT CCAGG tat 2P (SEQ ID NO:18): GGAGA TGCCT AAGGC TTTTG enva (SEQ ID NO:19): TGTTC CTTGG GTTCT TG envb (SEQ ID NO:20): GAGTT TTCCA GAGCA ACCCC sk68 (SEQ ID NO:21): AGCAG CAGGA AGCAC TATGG sk69 (SEQ ID NO:22): GCCCC AGACT GTGAG TTGCA ACAG 5v3e (SEQ ID NO:23): GCACA GTACA ATGTA CACAT GG 3v3e (SEQ ID NO:24): CAGTA GAAAA ATTCC CCTCC AC 5v3degi (SEQ ID NO:25): TCAGG ATCCA TGGGC AGTCT AGCAG AAGAA G 3v3degi (SEQ ID NO:26): ATGCT CGAGA ACTGC AGCAT CGATT CTGGG TCCCC TCCTG AG 3v3longdegi (SEQ ID NO:27): CGAGA ACTGC AGCAT CGATG CTGCT CCCAA GAACC CAAGG 3v3longext (SEQ ID NO:28): GGAGC TGCTT GATGC CCCAG A gagdi (SEQ ID NO:29): TGATG ACAGC ATGTC AGGGA GT pol e (SEQ ID NO:30): GCTGA CATTT ATCAC AGCTG GCTAC Amplifications which were weak as compared with those for HIV-1, but nevertheless of the same intensity as those for the HIV-2 isolate (MVP-11971/87) employed, were obtained with gag c (SEQ ID NO:31): TATCA CCTAG AACTT TAAAT GCATG GG gag d (SEQ ID NO:32): AGTCC CTGAC ATGCT GTCAT CA env c (SEQ ID NO:33): GTGGA GGGGA ATTTT TCTAC TG env d (SEQ ID NO:34): CCTGC TGCTC CCAAG AACCC AAGG.

The so-called Western blot (immunoblot) is a common method for detecting HIV antibodies. In this method, the viral proteins are fractionated by gel electrophoresis and then transferred to a membrane. The membranes provided with the transferred proteins are then brought into contact with sera from the patients to be investigated. If antibodies against the viral proteins are present, these antibodies will bind to the proteins. After the membranes have been washed, only antibodies which are specific for the viral proteins will remain. The antibodies are then rendered visible using antiantibodies which, as a rule, are coupled to an enzyme which catalyzes a color reaction. In this way, the bands of the viral proteins can be rendered visible.

The virus MVP-5180/91 (SEQ ID NO:56) according to the invention exhibits two significant and important differences from the HIV-1 and HIV-2 viruses in a Western blot. HIV-1 regularly shows a strong band, which is attributable to protein p 24, and a very weak band, which is often scarcely visible and which is attributable to protein p 23. HIV-2 exhibits a strong band, which is attributable to protein p 25, and sometimes a weak band, which is attributable to protein p 23. In contrast to this, the MVP-5180/91 (SEQ ID NO:56) virus according to the invention exhibits two bands of approximately equal strength, corresponding to proteins p 24 and p 25.

A further significant difference exists in the bands which are attributable to reverse transcriptase. HIV-1 shows one band (p 53) which corresponds to reverse transcriptase and one band (p 66) which corresponds to reverse transcriptase bound to RNAse H. In the case of HIV-2, the reverse transcriptase corresponds to protein p 55 and, if it is bound to RNAse H, to protein p 68. By contrast, MPV-5180/91 (SEQ ID NO:56) according to the invention exhibits one band at protein p 48, which corresponds to reverse transcriptase, and one band, at protein p 60, which corresponds to reverse transcriptase bound to RNAse H. It can be deduced from these results that the reverse transcriptase of MVP-5180/91 (SEQ ID NO:56) has a molecular weight which is roughly between 3 and 7 kilodaltons less than that of the reverse transcriptases of HIV-1 and HIV-2. The reverse transcriptase of MVP-5180 consequently has a molecular weight which is roughly between 4,500 daltons and 5,500 daltons less than that of the reverse transcriptase of HIV-1 or HIV-2.

It was discovered that anti-env antibodies could only be detected weakly in the sera of German patients exhibiting signs of immunodeficiency when the MVP-5180/91 (SEQ ID NO:56) virus according to the invention was used, whereas the sera reacted strongly if an HIV-1 virus was used instead of the virus according to the invention. This stronger detection reaction was located in the gp 41 protein, in particular. In the experiments, serum panels were compared which on the one hand derived from German patients and on the other from African patients showing signs of immune deficiency.

The abovementioned characteristics are indicative of those virus variants which correspond to MVP-5180/91 (SEQ ID NO:56) according to the invention. Therefore, the virus according to the invention, or variants thereof, can be obtained by isolating immunodeficiency viruses from heparinized donor blood derived from persons who exhibit signs of immune deficiency and who preferably originate from Africa.

Since the virus possessing the abovementioned properties has been isolated, the cloning of a cDNA can be carried out in the following manner: the virus is precipitated from an appropriately large quantity of culture (about 1 l ) and then taken up in phosphate-buffered sodium chloride solution. It is then pelleted through a (20% strength) sucrose cushion. The virus pellet can be suspended in 6 M guanidinium chloride in 20 mM dithiothreitol and 0.5% Nonidet P 40. CsCl is added to bring its concentration to 2 molar and the solution containing the disrupted virus is transferred to a cesium chloride cushion. The viral RNA is then pelleted by centrifugation, and subsequently dissolved, extracted with phenol and precipitated with ethanol and lithium chloride. Synthesis of the first cDNA strand is carried out on the viral RNA, or parts thereof, using an oligo(dT) primer. The synthesis can be carried out using a commercially available kit and adding reverse transcriptase. To synthesize the second strand, the RNA strand of the RNA/DNA hybrid is digested with RNase H, and the second strand is then synthesized using *E. coli* DNA polymerase I. Blunt ends can then be produced using T4 DNA polymerase and these ends can be joined to suitable linkers for restriction cleavage sites. Following restriction digestion with the appropriate restriction endonuclease, the cDNA fragment is isolated from an agarose gel and ligated to a vector which has previously been cut in an appropriate manner. The vector containing the cDNA insert can then be used for transforming competent *E. coli* cells. The colonies which are obtained are then transferred to membranes, lysed and denatured, and then finally detected by hybridization with nucleic acid labeled with digoxigenin or biotin. Once the corresponding cDNA has been prepared by genetic manipulation, it is possible to isolate the desired DNA fragments originating from the retrovirus. By incorporating these fragments into suitable expression vectors, the desired protein or protein fragment can then be expressed and employed for the diagnostic tests.

As an alternative to the stated method, the immunodeficiency virus can be cloned with the aid of PCR technology, it being possible to use the abovementioned primers.

The similarity between different virus isolates can be expressed by the degree of homology between the nucleic acid or protein sequences. 50% homology means, for example, that 50 out of 100 nucleotides or amino acid positions in the sequences correspond to each other. The homology of proteins is determined by sequence analysis. Homologous DNA sequences can also be identified by the hybridization technique.

In accordance with the invention, a part of the coat protein was initially sequenced and it was ascertained that this sequence possessed only relatively slight homology to the corresponding sequences from viruses of the HIV type. On the basis of a comparison with HIV sequences, which was carried out using data banks, it was established, in relation to the gp 41 region in particular, that the homology was at most 66% (nucleotide sequence).

In addition to this, the region was sequenced which encodes gp 41. This sequence is presented in Tables 1 and 3. Table 1 includes DNA SEQ ID NO:37, DNA SEQ ID NO:38, and amino acid SEQ ID NO:39. Table 3 includes DNA SEQ ID NO:44, DNA SEQ ID NO:45, and amino acid SEQ ID NO:46.

The present invention therefore relates to those viruses which possess an homology of more than 66%, preferably 75% and particularly preferably 85%, to the HIV virus, MVP-5180/91 (SEQ ID NO:56), according to the invention, based on the nucleotide sequence in Table 1 (SEQ ID NO:37; SEQ ID NO:38) and/or in Table 3 (SEQ ID NO:44; SEQ ID NO:45).

Furthermore, the present invention relates to those viruses which possess an homology of more than 66%, preferably 75% and particularly preferably 85%, to partial sequences of the nucleotide sequence presented in Table 3 (SEQ ID NO:44; SEQ ID NO:45), which sequences are at least 50, preferably 100, nucleotides long. This corresponds to a length of the peptides of at least 16, and preferably of at least 33, amino acids.

The sequence of the virus according to the invention differs from that of previously known viruses. The present invention therefore relates to those viruses, and corresponding DNA and amino acid sequences, which correspond to a large extent to the sequence of the virus according to the invention, the degree of deviation being established by the degree of homology. An homology of, for example, more than 85% denotes, therefore, that those sequences are included which have in at least 85 of 100 nucleotides or amino acids the same nucleotides or amino acids, respectively, while the remainder can be different. When establishing homology, the two sequences are compared in such a way that the greatest possible number of nucleotides or amino acids corresponding to each other are placed in congruence.

The (almost) complete sequence, given as the DNA sequence of the virus according to the invention, is reproduced in FIG. 4 and included as DNA SEQ ID NO:56. In this context, the present invention relates to viruses which possess the sequence according to FIG. 4 (SEQ ID NO:56), and variants thereof which possess a high degree of homology with the sequence of FIG. 4 (SEQ ID NO:56), as well as proteins, polypeptides and oligopeptides derived therefrom which can be used diagnostically or can be employed as vaccines.

Using the isolated sequence as a basis, immunodominant epitopes (peptides) can be designed and synthesized. Since the nucleic acid sequence of the virus is known, the person skilled in the art can derive the amino acid sequence from this known sequence. A constituent region of the amino acid sequence is given in Table 3 (SEQ ID NO:46). The present invention also relates, therefore, to antigens, i.e. proteins, oligopeptides or polypeptides, which can be prepared with the aid of the information disclosed in FIG. 4 (SEQ ID NO:56) and Table 3 (SEQ ID NO:44; SEQ ID NO:45, and SEQ ID NO:46). These antigens, proteins, polypeptides and oligopeptides possess amino acid sequences which can either be derived from FIG. 4 (SEQ ID NO:56) or are given in Table 3 (SEQ ID NO:46). The antigens or peptides can possess relatively short constituent sequences of an amino acid sequence which is reproduced in Table 3 (SEQ ID NO:46) or which can be derived from FIG. 4 (SEQ ID NO:56). This amino acid sequence is at least 6, preferably at least 10 and particularly preferably at least 15, amino acids in length. These peptides can be prepared not only with the aid of recombinant technology but also using synthetic methods. A suitable preparation route is solid-phase synthesis of the Merrifield type. Further description of this technique, and of other processes known to the state of the art, can be found in the literature, e.g. M. Bodansky, et al., Peptide Synthesis, John Wiley & Sons, 2nd Edition 1976.

In the diagnostic tests, a serum sample from the person to be investigated is brought into contact with the protein chains of one or more proteins or glycoproteins (which can be expressed in eukaryotic cell lines), or parts thereof, which originate from MVP-5180/91 (SEQ ID NO:56). Test processes which are preferred include immunofluorescence or immunoenzymatic test processes (e.g. ELISA or immunoblot).

In the immunoenzymatic tests (ELISA), antigen originating from MVP-5180/91 (SEQ ID NO:56) or a variant thereof, for example, can be bound to the walls of microtiter plates. The dosage used in this context depends to an important degree on the test system and the treatment of the microtiter plates. Serum or dilutions of serum deriving from the person to be investigated are then added to the wells of the microtiter plates. After a predetermined incubation time, the plate is washed and specific immunocomplexes are detected by antibodies which bind specifically to human immunoglobulins and which had previously been linked to an enzyme, for example horseradish peroxidase, alkaline phosphatase, etc., or to enzyme-labeled antigen. These enzymes are able to convert a colorless substrate into a strongly colored product, and the presence of specific anti-HIV antibodies can be gathered from the strength of the coloration. A further option for using the virus according to the invention in test systems is its use in Western blots.

Even if the preparation of vaccines against immunodeficiency diseases is proving to be extremely difficult, this virus, too, or parts thereof, i.e. immunodominant epitopes and inducers of cellular immunity, or antigens prepared by genetic manipulation, can still be used for developing and preparing vaccines.

EXAMPLE 1

The immunodeficiency virus according to the invention, MVP-5180/91 (SEQ ID NO:56), was isolated from the blood of a female patient exhibiting signs of immune deficiency. To do this, peripheral mononuclear cells (peripheral blood lymphocytes, PBL) and peripheral lymphocytes from the blood (PBL) of a donor who was not infected with HIV were stimulated with phytohemagglutinin and maintained in culture. For this purpose, use was made of the customary medium RPMI 1640 containing 10% fetal calf serum. The culture conditions are described in Landay A. et al., J. Inf. Dis., 161 (1990) pp. 706–710. The formation of giant cells was then observed under the microscope. The production of HIV viruses was ascertained by determining the p 24 antigen using the test which can be purchased from Abbott. An additional test for determining the growth of the viruses consisted of the test using particle-bound reverse transcriptase (Eberle J., Seibl R., J. Virol. Methods 40, 1992, pp. 347–356). The growth of the viruses was therefore determined once or twice a week on the basis of the enzymatic activities in the culture supernatant, in order to monitor virus production. New donor lymphocytes were added once a week.

Once it was possible to observe HIV virus multiplication, fresh peripheral lymphocytes from the blood (PBL) of healthy donors, who were not infected with HIV, were infected with supernatant from the first culture. This step was repeated and the supernatant was then used to infect H 9 and HUT 78 cells. In this way, it was possible to achieve permanent production of the immunodeficiency virus. The virus was deposited with the ECACC under No. V 920 92 318.

EXAMPLE 2

So-called Western blot or immunoblot is currently a standard method for detecting HIV infections. Various sera were examined in accordance with the procedure described by Gürtler et al. in J. Virol. Meth. 15 (1987) pp. 11–23. In doing this, sera from German patients were compared with sera which had been obtained from African patients. The following results were obtained:

| Virus type | German sera | African sera |
|---|---|---|
| HIV-1, virus isolated from German patients | strong reaction | strong reaction using gp 41 |
| MVP-5180/91 (SEQ ID NO:56) | no reaction to weak reaction using gp 41 | strong reaction |

The results presented above demonstrate that a virus of the HIV-1 type isolated from German patients may possibly, if used for detecting HIV infections, fail to provide unambiguous results if the patient was infected with a virus corresponding to MVP-5180/91 (SEQ ID NO:56) according to the invention. It is assumed here that those viruses can be detected using the virus according to the invention which possess at least about 85% homology, based on the total genome, with the virus according to the invention.

EXAMPLE 3

Further Western blots were carried out in accordance with the procedure indicated in Example 2. The results are presented in the enclosed FIG. 3. In this test, the viral protein of the immunodeficiency virus MVP-5180/91 (SEQ ID NO:56) according to the invention, in the one case, and the viral protein of an HIV-1 type virus (MVP-899), in the other, was fractionated by gel electrophoresis and then transferred to cellulose filters. These filter strips were incubated with the sera from different patients and the specific antibodies were then rendered visible by a color reaction. The left half of the figure with the heading MVP-5180 shows the immunodeficiency virus according to the invention. The right half of the figure shows a virus (MVP-899), which is an HIV-1 virus, isolated from a German donor.

Figure 3:
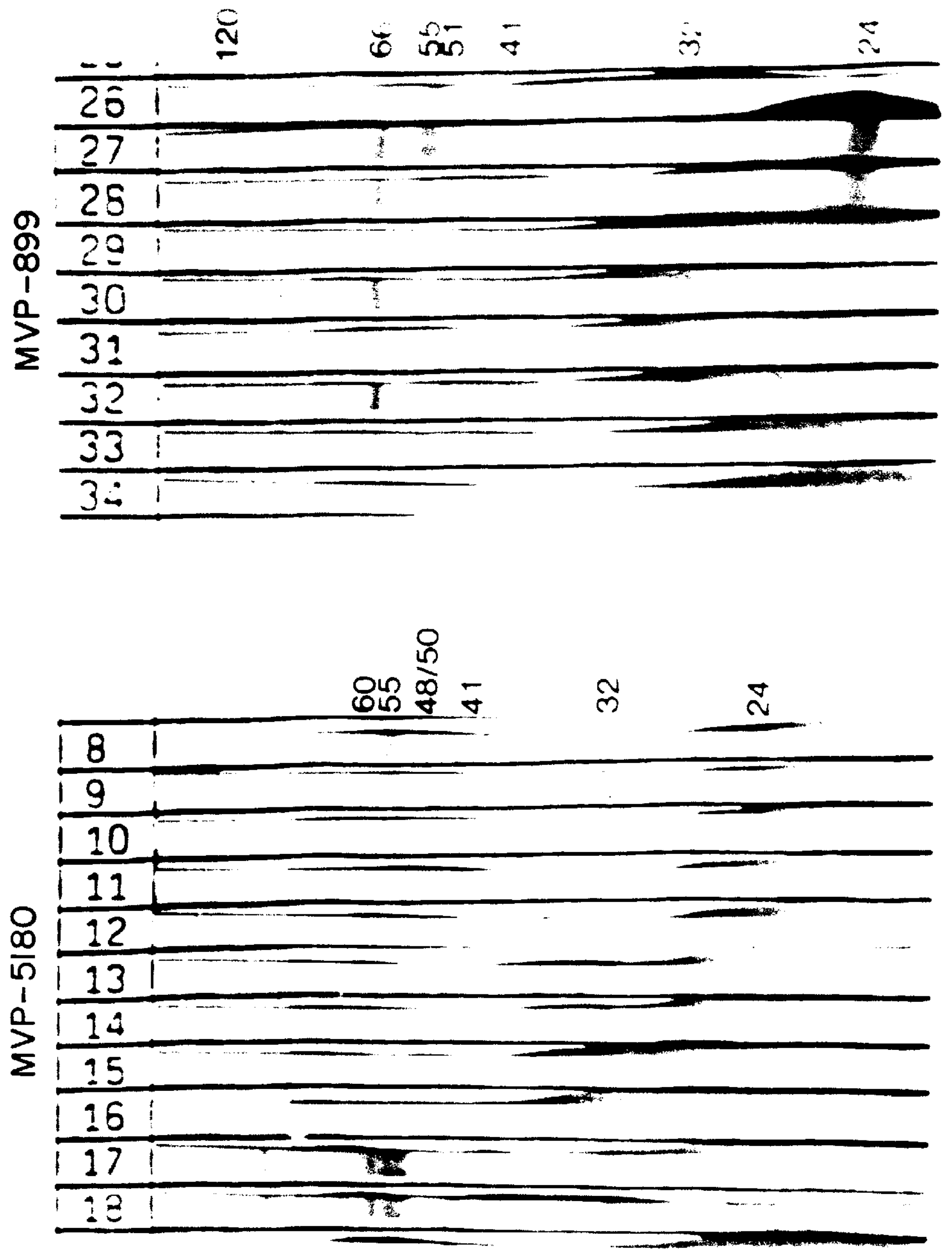
FIG. 3 depicts a western blot of MVP-5180/91 and HIV-1, isolated from German patients.

In FIG. 3, the same sera (from German patients) were in each case reacted with two respective filter strips, the numbers 8 and 26; 9 and 27; 10 and 28; 11 and 29; 12 and 30; 13 and 31; 14 and 32; 15 and 33, and 16 and 34 indicating the same sera. Sera from African patients were employed in the Western blots having the numbers 17 and 18. The numbers on the right hand margins indicate the approximate molecular weights in thousands (KD).

FIG. 3 shows clearly that sera from German patients only react very weakly with the immunodeficiency virus according to the invention in a Western blot using gp 41. By contrast, sera from African patients react very strongly with the immunodeficiency virus according to the invention. FIG. 3 makes it clear, therefore, that when the immunodeficiency virus according to the invention is used those immunodeficiency infections can be detected which only yield questionable, i.e. not unambiguously positive, results when an HIV-1 or HIV-2 virus is used. This option for detection can be of far-reaching diagnostic importance since, in those cases in which only questionable results are obtained in a Western blot, it cannot be established with unambiguous certainty whether an infection with an immunodeficiency virus is present. However, if the immunodeficiency virus according to the invention can be used to assign such questionable results to an infection with a virus of the type according to the invention, this then represents a substantial diagnostic advance.

EXAMPLE 4

DNA isolation, amplification and structural characterization of sections of the genome of the HIV isolate MVP-5180/91 (SEQ ID NO:56).

Genomic DNA from HUT 78 cells infected with MVP-5180/91 (SEQ ID NO:56) was isolated by standard methods.

In order to characterize regions of the genome of the isolate MVP-5180/91 (SEQ ID NO:56), PCR (polymerase chain reaction) experiments were carried out using a primer pair from the region of the coat protein gp 41. The PCR experiments were carried out in accordance with the method of Saiki et al. (Saiki et al., Science 239: 487–491, 1988) using the following modifications: for the amplification of regions of HIV-specific DNA, 5 μl of genomic DNA from HUT 78 cells infected with MVP-5180/91 (SEQ ID NO:56) were pipetted into a 100 μl reaction mixture (0.25 mM dNTP, in each case 1 μm primer 1 and primer 2, 10 mM Tris HCl, pH 8.3, 50 mM KCl, 1.5 $MgCl_2$, 0.001% gelatin, 2.5 units of Taq polymerase (Perkin Elmer)), and amplification was then carried out in accordance with the following temperature program: 1. initial denaturation: 3' 95° C., 2. amplification: 90" 94° C., 60" 56° C., 90", 72° C. (30 cycles).

The primers used for the PCR and for nucleotide sequencing were synthesized on a Biosearch 8750 oligonucleotide synthesizer.

Primer 1 (SEQ ID NO:35): AGC AGC AGG AAG CAC TAT GG (coordinates from HIV-1 isolate HXB2: bases 7795–7814, corresponds to primer sk 68) (SEQ ID NO:21)

Primer 2 (SEQ ID NO:36): GAG TTT TCC AGA GCA ACC CC (coordinates from HIV-1 isolate HXB2: bases 8003–8022, corresponds to primer env b (SEQ ID NO:20).

The amplified DNA was fractionated on a 3% "Nusieve" agarose gel (from Biozyme) and the amplified fragment was then cut out and an equal volume of buffer (1*TBE (0.09 M Tris borate, 0.002 M EDTA, pH 8.0) was added to it. After incubating the DNA/agarose mixture at 70° C. for 10 minutes, and subsequently extracting with phenol, the DNA was precipitated from the aqueous phase by adding 1/10 vol of 3 M NaAc, pH 5.5, and 2 vol of ethanol and storing at −20° C. for 15', and then subsequently pelleted in a centrifuge (Eppendorf) (13,000 rpm, 10', 4° C.). The pelleted DNA was dried and taken up in water, and then, after photometric determination of the DNA concentration at 260 nm in a spectrophotometer (Beckman), sequenced by the Sanger method (F. Sanger, Proc. Natl. Acad,. Sci., 74: 5463, 1977). Instead of sequencing with Klenow DNA polymerase, the sequencing reaction was carried out using a kit from Applied Biosystems ("Taq dye deoxy terminator cycle sequencing", order No.: 401150). Primer 1 (SEQ ID NO:35) or primer 2 (SEQ ID NO:36) (in each case 1 μM) was employed as primers in separate sequencing reactions. The sequencing reaction was analysed on a 373A DNA sequencing apparatus (Applied Biosystems) in accordance with the instructions of the apparatus manufacturer.

The nucleotide sequence of the amplified DNA region, and the amino acid sequence deduced from it, are presented in Table 1. Table 1 includes the DNA sequences SEQ ID NO:37 and SEQ ID NO:38, as well as amino acid SEQ ID NO:39. The top line in Table 1 corresponds to SEQ ID NO:37, the middle line corresponds to SEQ ID NO:38, and the bottom line corresponds to the amino acid SEQ ID NO:39.

TABLE 1

```
GCGCAGCGGCAACAGCGCTGACGGTACGGACCCACAGTGTACTGAAGGGTATAGTGCAAC
----------+---------+----------+----------+----------+----------+
CGCGTCGCCGTTGTCGCGACTGCCATGCCTGGGTGTCACATGACTTCCCATATCACGTTG

  A  A  A  T  A  L  T  V  R  T  H  S  V  L  K  G  I  V  Q  Q

AGCAGGACAACCTGCTGAGAGCGATACAGGCCCAGCAACACTTGCTGAGGTTATCTGTAT
---------+---------+----------+-----+----+----------+----------+
TCGTCCTGTTGGACGACTCTCGCTATGTCCGGGTCGTTGTGAACGACTCCAATAGACATA

  Q  D  N  L  L  R  A  I  Q  A  Q  Q  H  L  L  R  L  S  V  W

GGGGTATTAGACAACTCCGAGCTCGCCTGCAAGCCTTAGAAACCCTTATACAGAATCAGC
---------+---------+----------+----------+----------+----------+
CCCCATAATCTGTTGAGGCTCGAGCGGACGTTCGGAATCTTTGGGAATATGTCTTAGTCG

  G  I  R  Q  L  R  A  R  L  Q  A  L  E  T  L  I  Q  N  Q  Q

AACGCCTAAACCTAT
---------+-----   195
TTGCGGATTTGGATA

  R  L  N  L
```

EXAMPLE 5

The found nucleotide sequence from Table 1 was examined for homologous sequences in the GENEBANK database (Release 72, June 1992) using the GCG computer program (Genetic Computer Group, Inc., Wisconsin USA, Version 7.1, March 1992). Most of the nucleotide sequences of immunodeficient viruses of human origin and of isolates from primates known by July 1992 are contained in this database.

The highest homology shown by the nucleotide sequence from Table 1, of 66%, is to a chimpanzee isolate. The highest homology shown by the investigated DNA sequence from MVP-5180/91 (SEQ ID NO:56) to HIV-1 isolates is 64%. The DNA from Table 1 is 56% homologous to HIV-2 isolates. Apart from the chimpanzee isolate sequence, the best homology between the nucleotide sequence from Table 1 (SEQ ID NO:37; SEQ ID NO:38) and segments of DNA from primate isolates (SIV: simian immunodeficiency virus) is found with a DNA sequence encoding a part of the coat protein region from the SIV isolate (African long-tailed monkey) TYO-1. The homology is 61.5%.

EXAMPLE 6

The found amino acid sequence from Table 1 (SEQ ID NO:39) was examined for homologous sequences in the SWISSPROT protein database (Release Jun. 22, 1992) using the GCG computer program. Most of the protein sequences of immunodeficiency viruses of human origin and of isolates from primates known by June 1992 are contained in this database.

The highest homology shown by the amino acid sequence from Table 1 (SEQ ID NO:39), of 62.5%, is to a segment of coat protein from the abovementioned chimpanzee isolate. The best homology among HIV-1 coat proteins to the amino acid sequence from Table 1 (SEQ ID NO:39) is found in the isolate HIV-1 Mal. The homology is 59%. The highest homology of the amino acid sequence from Table 1 (SEQ ID NO:39) to HIV-2 coat proteins is 52% (isolate HIV-2 Rod). Since HIV-1 and HIV-2 isolates, themselves, are at most only 64% identical in the corresponding protein segment, the MVP-5180/91 (SEQ ID NO:56) isolate appears to be an HIV variant which clearly differs structurally from HIV-1 and HIV-2 and thus represents an example of an independent group of HIV viruses.

The amino acid sequence of the amplified region of DNA (Table 1; SEQ ID NO:39) from the HIV isolate MVP-5180/91 (SEQ ID NO:56) overlaps an immunodiagnostically important region of the coat protein gp 41 from HIV-1 (amino acids 584–618*) (Table 2, which includes SEQ ID NO:61 as the top line and SEQ ID NO:63 as the bottom line) (Gnann et al., J. Inf. Dis. 156: 261–267, 1987; Norrby et al., Nature, 329: 248–250, 1987).

Corresponding amino acid regions from the coat proteins of HIV-2 and SIV are likewise immunodiagnostically conserved (Gnann et al., Science, pp. 1346–1349, 1987). Thus, peptides from this coat protein region of HIV-1 and HIV-2 are employed as solid-phase antigens in many commercially available HIV-1/2 antibody screening tests. Approximately 99% of the anti-HIV-1 and anti-HIV-2 positive sera can be identified by them.

The amino acid region of the MVP-5180/91 coat protein (Table 1) could be of serodiagnostic importance owing to the overlap with the immunodiagnostically important region from gp 41. This would be the case particularly if antisera from HIV-infected patients failed to react positively with any of the commercially available antibody screening tests. In these cases, the infection could be with a virus which was closely related to MVP-5180/91 (SEQ ID NO:56).

TABLE 2

(includes SEQ ID NO:61 as the top line and SEQ ID NO:63 as the bottom line)

```
         .         .         .         .
........RILAVERYLKDQQLLGIWGCSGKLICTTAVPWNAS
        |: |:| .:.:|| |.:
WGIRQLRARLQALETLIQNQQRLNL..................
```

EXAMPLE 7

DNA isolation, amplification and structural characterization of genome segments from the HIV isolate MVP-5180/91 (SEQ ID NO:56) (encoding gp 41).

Genomic DNA from MVP-5180/91 (SEQ ID NO:56)-infected HUT 78 cells was isolated as described.

In order to characterize genomic regions of the isolate MVP-5180/91, PCR (polymerase chain reaction) experiments were carried out using primer pairs from the gp 41 coat protein region. PCR (Saiki et al., Science 239: 487–491, 1988) and inverse PCR (Triglia et al., Nucl. Acids, Res. 16: 8186, 1988) were carried out with the following modifications:

1. PCR

For the amplification of HIV-specific DNA regions, 5 μl (218 μg/ml) of genomic DNA from MVP-5180/91-infected HUT 78 cells were pipetted into a 100 μl reaction mixture (0.25 mM dNTP, in each case 1 μm primer 163env (SEQ ID NO:40) and primer envend (SEQ ID NO:41), 10 mM Tris HCl, pH 8.3, 50 mM KCl, 1.5 mM $MgCl_2$, 0.001% gelatin, 2.5 units of Taq polymerase (Perkin Elmer)), and amplification was then carried out in accordance with the following temperature program: 1. initial denaturation: 3 min. 95° C., 2. amplification: 90 sec. 94° C., 60 sec. 56° C., 90 sec. 72° C. (30 cycles).

2. Inverse PCR

The 5' region of gp 41 (N terminus) and the 3' sequence of gp 120 were amplified by means of "inverse PCR". For this, 100 μl of a genomic DNA preparation (218 μg/ml) from MVP-5180/91-infected HUT 78 cells were digested at 37° C. for 1 hour in a final volume of 200 μl using 10 units of the restriction endonuclease Sau3a. The DNA was subsequently extracted with phenol and then precipitated using sodium acetate (final concentration 300 mM) and 2.5 volumes of ethanol, with storage at −70° C. for 10 min, and then centrifuged down in an Eppendorf centrifuge; the pellet was then dried and resuspended in 890 μl of distilled water. Following addition of 100 μl of ligase buffer (50 mM Tris HCl, pH 7.8, 10 mM $MgCl_2$, 10 mM DTT, 1 mM ATP, 25 μg/ml bovine serum albumin) and 10 μl of T4 DNA ligase (from Boehringer, Mannheim), the DNA fragments were ligated at room temperature for 3 hours and then extracted with phenol once again and precipitated with sodium acetate and ethanol as above. After centrifuging down and drying, the DNA was resuspended in 40 μl of distilled water and digested for 1 hour with 10 units of the restriction endonuclease SacI (from Boehringer, Mannheim). 5 μl of this mixture were then employed in a PCR experiment as described under "1. PCR". The primers 168i (SEQ ID NO:42) and 169i (SEQ ID NO:43) were used for the inverse PCR in place of primers 163env (SEQ ID NO:40) and envend (SEQ ID NO:41).

The primers 163env (SEQ ID NO:40), 168i (SEQ ID NO:42) and 169i (SEQ ID NO:43) were selected from that part of the sequence of the HIV isolate MVP-5180 (SEQ ID NO:56) which had already been elucidated (Example 4).

The primers used for the PCR/inverse PCR and the nucleotide sequencing were synthesized on a Biosearch 8750 oligonucleotide synthesizer, with the primers having the following sequences:

Primer 163env (SEQ ID NO:40): 5' CAG AAT CAG CAA CGC CTA AAC C 3'

Primer envend (SEQ ID NO:41): 5' GCC CTG TCT TAT TCT TCT AGG 3'

(position from HIV-1 isolate BH10: bases 8129-8109)

Primer 168i (SEQ ID NO:42): 5' GCC TGC AAG CCT TAG AAA CC 3'

Primer 169i (SEQ ID NO:43): 5' GCA CTA TAC CCT TCA GTA CAC TG 3'

The amplified DNA was fractionated on a 3% "Nusieve" agarose gel (from Biozyme) and the amplified fragment was then cut out and an equal volume of buffer (1*TBE (0.09 M Tris borate, 0.002 M EDTA, pH 8.0)) was added to it. After incubating the DNA/agarose mixture at 70° C. for 10 minutes, and subsequent phenol extraction, the DNA was precipitated from the aqueous phase by adding 1/10 vol of 3 M NaAc, pH 5.5, and 2 vol of ethanol, and storing at −20° C. for 15', and then pelleted in an Eppendorf centrifuge (13,000 rpm, 10', 4° C.). The pelleted DNA was dried and then taken up in water and sequenced by the method of Sanger (F. Sanger, Proc. Natl. Acad. Sci., 74: 5463, 1977) following photometric determination of the DNA concentration at 260 nm in a spectrophotometer (from Beckman). Instead of sequencing with Klenow DNA polymerase, the sequencing reaction was carried out using a kit from Applied Biosystems ("Taq dye deoxy terminator cycle sequencing", order No.: 401150). Primer 163env (SEQ ID NO:40) or primer envend (SEQ ID NO:41) (in each case 1 μM) was employed as the primer in separate sequencing reactions. The amplified DNA from the inverse PCR experiment was sequenced using primers 168i (SEQ ID NO:42) and 169i (SEQ ID NO:43). The sequencing reaction was analysed on an Applied Biosystems 373A DNA sequencing apparatus in accordance with the instructions of the apparatus manufacturer.

The nucleotide sequence of the amplified DNA region, and the amino acid sequence deduced from it, are presented in Table 3. Table 3 includes DNA sequences SEQ ID NO:44 and SEQ ID N0:45, as well as amino acid sequence SEQ ID NO:46. In Table 3, the top line corresponds to SEQ ID NO:44, the middle line corresponds to SEQ ID NO:45, and the bottom line represents amino acid sequence SEQ ID NO:46.

TABLE 3

```
    AAATGTCAAGACCAATAATAAACATTCACACCCCTCACAGGGAAAAAAGAGCAGTAGGAT
  1 ---------+---------+---------+---------+---------+---------+  60
    TTTACAGTTCTGGTTATTATTTGTAAGTGTGGGGAGTGTCCCTTTTTTCTCGTCATCCTA

      M  S  R  P  I  I  N  I  H  T  P  H  R  E  K  R |A  V  G  L
                                            gp120             gp41

    TGGGAATGCTATTCTTGGGGGTGCTAAGTGCAGCAGGTAGCACTATGGGCGCAGCGGCAA
 61 ---------+---------+---------+---------+---------+---------+  120
    ACCCTTACGATAAGAACCCCCACGATTCACGTCGTCCATCGTGATACCCGCGTCGCCGTT

      G  M  L  F  L  G  V  L  S  A  A  G  S  T  M  G  A  A  A  T

    CAGCGCTGACGGTACGGACCCACAGTGTACTGAAGGGTATAGTGCAACAGCAGGACAACC
121 ---------+---------+---------+---------+---------+---------+  180
    GTCGCGACTGCCATGCCTGGGTGTCACATGACTTCCCATATCACGTTGTCGTCCTGTTGG

      A  L  T  V  R  T  H  S  V  L  K  G  I  V  Q  Q  Q  D  N  L

    TGCTGAGAGCGATACAGGCCCAGCAACACTTGCTGAGGTTATCTGTATGGGGTATTAGAC
181 ---------+---------+---------+---------+---------+---------+  240
    ACGACTCTCGCTATGTCCGGGTCGTTGTGAACGACTCCAATAGACATACCCCATAATCTG

      L  R  A  I  Q  A  Q  Q  H  L  L  R  L  S  V  W  G  I  R  Q

    AACTCCGAGCTCGCCTGCAAGCCTTAGAAACCCTTATACAGAATCAGCAACGCCTAAACC
241 ---------+---------+---------+---------+---------+---------+  300
    TTGAGGCTCGAGCGGACGTTCGGAATCTTTGGGAATATGTCTTAGTCGTTGCGGATTTGG

      L  R  A  R  L  Q  A  L  E  T  L  I  Q  N  Q  Q  R  L  N  L

    TATGGGGCTGTAAAGGAAAACTAATCTGTTACACATCAGTAAAATGGAACACATCATGGT
301 ---------+---------+---------+---------+---------+---------+  360
    ATACCCCGACATTTCCTTTTGATTAGACAATGTGTAGTCATTTTACCTTGTGTAGTACCA

      W  G  C  K  G  K  L  I  C  Y  T  S  V  K  W  N  T  S  W  S

    CAGGAGGATATAATGATGACAGTATTTGGGACAACCTTACATGGCAGCAATGGGACCAAC
361 ---------+---------+---------+---------+---------+---------+  420
    GTCCTCCTATATTACTACTGTCATAAACCCTGTTGGAATGTACCGTCGTTACCCTGGTTG

      G  G  Y  N  D  D  S  I  W  D  N  L  T  W  Q  Q  W  D  Q  H

    ACATAAACAATGTAAGCTCCATTATATATGATGAAATACAAGCAGCACAAGACCAACAGG
421 ---------+---------+---------+---------+---------+---------+  480
    TGTATTTGTTACATTCGAGGTAATATATACTACTTTATGTTCGTCGTGTTCTGGTTGTCC

      I  N  N  V  S  S  I  I  Y  D  E  I  Q  A  A  Q  D  Q  Q  E

    AAAAGAATGTAAAAGCATTGTTGGAGCTAGATGAATGGGCCTCTCTTTGGAATTGGTTTG
481 ---------+---------+---------+---------+---------+---------+  540
    TTTTCTTACATTTTCGTAACAACCTCGATCTACTTACCCGGAGAGAAACCTTAACCAAAC

      K  N  V  K  A  L  L  E  L  D  E  W  A  S  L  W  N  W  F  D

    ACATAACTAAATGGTTGTGGTATATAAAAATAGCTATAATCATAGTGGGAGCACTAATAG
541 ---------+---------+---------+---------+---------+---------+  600
    TGTATTGATTTACCAACACCATATATTTTTATCGATATTAGTATCACCCTCGTGATTATC

      I  T  K  W  L  W  Y  I  K  I  A  I  I  I  V  G  A  L  I  G

    GTATAAGAGTTATCATGATAGTACTTAATCTAGTGAAGAACATTAGGCAGGGATATCAAC
601 ---------+---------+---------+---------+---------+---------+  660
    CATATTCTCAATAGTACTATCATGAATTAGATCACTTCTTGTAATCCGTCCCTATAGTTG

      I  R  V  I  M  I  V  L  N  L  V  K  N  I  R  Q  G  Y  Q  P

    CCCTCTCGTTGCAGATCCCTGTCCCACACCGGCAGGAAGCAGAAACGCCAGGAAGAACAG
661 ---------+---------+---------+---------+---------+---------+  720
    GGGAGAGCAACGTCTAGGGACAGGGTGTGGCCGTCCTTCGTCTTTGCGGTCCTTCTTGTC

      L  S  L  Q  I  P  V  P  H  R  Q  E  A  E  T  P  G  R  T  G

    GAGAAGAAGGTGGAGAAGGAGACAGGCCCAAGTGGACAGCCTTGCCACCAGGATTCTTGC
721 ---------+---------+---------+---------+---------+---------+  780
    CTCTTCTTCCACCTCTTCCTCTGTCCGGGTTCACCTGTCGGAACGGTGGTCCTAAGAACG

      E  E  G  G  E  G  D  R  P  K  W  T  A  L  P  P  G  F  L  Q
```

TABLE 3-continued

```
     AACAGTTGTACACGGATCTCAGGACAATAATCTTGTGGACTTACCACCTCTTGAGCAACT
 781 ---------+---------+---------+---------+---------+---------+   840
     TTGTCAACATGTGCCTAGAGTCCTGTTATTAGAACACCTGAATGGTGGAGAACTCGTTGA

       Q  L  Y  T  D  L  R  T  I  I  L  W  T  Y  H  L  L  S  N  L

     TAATATCAGGGATCCGGAGGCTGATCGACTACCTGGGACTGGGACTGTGGATCCTGGGAC
 841 ---------+---------+---------+---------+---------+---------+   900
     ATTATAGTCCCTAGGCCTCCGACTAGCTGATGGACCCTGACCCTGACACCTAGGACCCTG

       I  S  G  I  R  R  L  I  D  Y  L  G  L  G  L  W  I  L  G  Q

     AAAAGACAATTGAAGCTTGTAGACTTTGTGGAGCTGTAATGCAATATTGGCTACAAGAAT
 901 ---------+---------+---------+---------+---------+---------+   960
     TTTTCTGTTAACTTCGAACATCTGAAACACCTCGACATTACGTTATAACCGATGTTCTTA

       K  T  I  E  A  C  R  L  C  G  A  V  M  Q  Y  W  L  Q  E  L

     TGAAAAATAGTGCTACAAACCTGCTTGATACTATTGCAGTGTCAGTTGCCAATTGGACTG
 961 ---------+---------+---------+---------+---------+---------+  1020
     ACTTTTTATCACGATGTTTGGACGAACTATGATAACGTCACAGTCAACGGTTAACCTGAC

       K  N  S  A  T  N  L  L  D  T  I  A  V  S  V  A  N  W  T  D

     ACGGCATCATCTTAGGTCTACAAAGAATAGGACAAGG
1021 ---------+---------+---------+--------                         1057
     TGCCGTAGTAGAATCCAGATGTTTCTTATCCTGTTCC

       G  I  I  L  G  L  Q  R  I  G  Q
```

EXAMPLE 8

The found nucleotide sequence from Table 3 (SEQ ID NO:44; SEQ ID NO:45) was examined for homologous sequences in the GENEBANK database (Release 72, June 1992) using the GCG computer program (Genetic Computer Group, Inc. Wisconsin USA, version 7.1, March 1992). Most of the nucleotide sequences of immunodeficiency viruses of human origin and of isolates from primates known by July 1992 are contained in this database.

The highest homology of the nucleotide sequence from Table 3 (SEQ ID NO:44; SEQ ID NO:45) to an HIV-1 isolate is 62%. The DNA from Table 3 is 50% homologous to HIV-2 isolates.

The amino acid sequence deduced from the nucleotide sequence from Table 3 (SEQ ID NO:46) was examined for homologous sequences in the SWISSPROT protein database (Release Jun. 22, 1992) using the GCG computer program. Most of the protein sequences of immunodeficiency viruses of human origin and of isolates from primates known by June 1992 are contained in this database.

At best, the amino acid sequence from Table 3 (SEQ ID NO:46) is 54% homologous to the corresponding coat protein segment from a chimpanzee isolate CIV (SIVcpz) and 54.5% homologous to the HIV-1 isolate Mal. At best, the amino acid sequence from Table 3 (SEQ ID NO:46) is 34% homologous to HIV-2 coat proteins (isolate HIV-2 D194).

If, by contrast, the gp 41 amino acid sequence of HIV-1 is compared with the HIV-1 gp 41 sequence present in the SWISSPROT database, the highest homology is, as expected, almost 100%, and the lowest 78%.

These clear structural differences between the sequence region from Table 3 and the corresponding segment from HIV-1 and HIV-2 suggest that isolate MVP-5180/91 (SEQ ID NO:56) is an HIV variant which clearly differs structurally from HIV-1 and HIV-2. It is possible that MVP-5180/91 (SEQ ID NO:56) should be assigned to a separate group of HIV viruses which differ from HIV-1 and HIV-2.

The peptide from amino acid 584 to amino acid 618 of the HIV-1 coat protein region (SEQ ID NO:61) is of particular serodiagnostic interest (numbering in accordance with Wain Hobson et al., Cell 40: 9–17, 1985; Gnann et al., J. Inf. Dis. 156: 261–267, 1987; Norrby et al., Nature, 329: 248–250, 1987). Corresponding amino acid regions from the coat proteins of HIV-2 and SIV are likewise immunodiagnostically conserved (Gnann et al., Science, pp. 1346–1349, 1987). Thus, peptides from this coat protein region of HIV-1 and HIV-2 are employed as solid-phase antigens in many commercially available HIV-1/2 antibody screening tests. Using them, approximately 99% of the anti-HIV-1 and anti-HIV-2-positive sera can be identified.

The corresponding amino acid region of the MVP-5180/91 coat protein (Table 4), as well as the whole gp 41 of this isolate, could be of serodiagnostic importance, particularly if antisera from HIV-infected patients either did not react at all or only reacted weakly in commercially available antibody screening tests. In these cases, the infection could be due to a virus which is closely related to MVP-5180/91 (SEQ ID NO:56).

Table 4 includes SEQ ID NO:61, which is designated as line 1, and also highlights in line 2 the points of difference from the amino acid sequence designated SEQ ID NO:62. Amino acid sequence SEQ ID NO:62 appears in full following Table 4.

TABLE 4

```
1  RILAVERYLKDQQLLGIWGCSGKLICTTAVPWNAS
2   LQ L TLIQN R NL    K    Y S K T
```

1 = HIV-1 amino acid sequence from gp 41 = (SEQ ID NO:61)
2 = MVP-5180 sequence from gp 41. Only differences from the HIV-1 sequence are indicated.

The peptide, which was found with the aid of information deriving from MVP-5180, thus has the amino acid sequence (SEQ ID NO:62): RLQALETLIQNQQRLNLWGCKGKLI-CYTSVKWNTS.

The present invention therefore relates to peptides which can be prepared recombinantly or synthetically and have the sequence indicated above, or a constituent sequence thereof, the constituent sequences having at least 6 consecutive amino acids, preferably 9 and particularly preferably 12 consecutive amino acids.

EXAMPLE 9

Cloning of the whole genome of the HIV isolate MVP-5180 (SEQ ID NO:56)

a) Preparation of a Genomic Library

Genomic DNA from MVP-5180-infected HUT 78 cells was isolated as described.

300 μg of this DNA were incubated for 45 min in a volume of 770 μl together with 0.24 U of the restriction enzyme Sau3A. The DNA, which was only partially cut in this incubation, was subsequently size-fractionated on a 0.7% agarose gel (low melting agarose, Nusieve) and fragments of between 10 and 21 kb were cut out. The agarose was melted at 70° C. for 10 min and the same volume of buffer (1*TBE, 0.2 M NaCl) was then added to it. Subsequently, after having extracted twice with phenol and once with chloroform, the DNA was precipitated by adding 1/10 vol. of 3 M sodium acetate solution (pH 5.9) and 2.5 vol. of ethanol, and storing at −70° C. for 10 min. The precipitated DNA was centrifuged down and dried and then dissolved in water at a concentration of 1 μg/μl.

The yield of size-fractionated DNA was about 60 μg. 5 μg of this DNA were incubated at 37° C. for 20 min in an appropriate buffer together with 1 U of alkaline phosphatase. In this way, the risk of multiple insertions of size-fractionated DNA was reduced by eliminating the 5'-terminal phosphate radical. The phosphatase treatment was stopped by extracting with phenol and the DNA was precipitated as above and then ligated at 15° C. for 12 hours together with 1 μg of the vector (2 DASH, BamHI-cut, Stratagene No.: 247611) in a total volume of 6 μl using 2 Weiss units of Lambda T4 ligase. Following completed ligation, the DNA was packaged into phage coats using a packaging kit (Gigapack II Gold, Stratagene No.: 247611) precisely in accordance with the manufacturer's instructions.

b) Radioactive Labeling of the DNA Probe.

The "random-primed DNA labeling kit" from Boehringer Mannheim (No.: 713 023) was employed for the labeling. The PCR product was labeled which was obtained as described in Example 3 using the primers sk68 (SEQ ID NO:21) and envb (SEQ ID NO:20). 1 μg of this DNA was denatured by 2*5 min of boiling and subsequent cooling in ice water. 50 mCi [a- $^{32}$p]-dCTP (NEN, No.: NEX-053H) were added for the labeling. Other ingredients were added by pipette in accordance with the manufacturer's instructions. Following a 30 min incubation at 37° C., the DNA, which was now radioactively labeled, was precipitated.

c) Screening the Phage Library 20,000 pfu (plaque-forming units) of the library in 100 μl of SM buffer (5.8 g of NaCl, 2 g of $MgSO_4$, 50 ml of 1 M Tris, pH 7.5, and 5 ml of a 2% gelatin solution, dissolved in 1 l of $H_2O$) were added to 200 μl of a culture (strain SRB(P2) [Stratagene, No.: 247611] in LB medium, which contained 10 mM $MgSO_4$ and 0.2% maltose) which had been grown at 30° C. overnight; the phages were adsorbed to the bacteria at 37° C. for 20 min and 7.5 ml of top agarose, which had been cooled to 55° C., was then mixed in and the whole sample was distributed on a pre-warmed LB agar plate of 14 cm diameter. The plaques achieved confluence after about 8 hours. After that, nitrocellulose filters were laid on the plates for a few minutes and were marked asymmetrically. After having been carefully lifted from the plates, the filters were denatured for 2 min (0.5 M NaOH, 1.5 M NaCl) and then neutralized for 5 min (0.5 M Tris, pH 8, 1.5 M NaCl). The filters were subsequently baked at 80° C. for 60 min and could then be hybridized to the probe. For the prehybridization, the filters were incubated at 42° C. for 2–3 h, while shaking, in 15 ml of hybridization solution (50% formamide, 0.5% SDS, 5*SSPE, 5*Denhardt's solution and 0.1 mg/ml salmon sperm DNA) per filter. The [$^{32}$p]-labeled DNA probes were denatured at 100° C. for 2–5 min and then cooled on ice; they were then added to the prehybridization solution and hybridization was carried out at 42° C. for 12 hours. Subsequently, the filters were washed at 60° C., firstly with 2*SSC/0.1% SDS and then with 0.2*SSC/0.1% SDS. After the filters had been dried, hybridization signals were detected using the X-ray film X-OMAT™AR (Kodak).

Following elution in SM buffer, those plaques to which it was possible to assign a signal were individually separated in further dilution steps.

It was possible to identify the clone described below following screening of 2*$10^6$ plaques.

d) Isolation of the phage DNA and subcloning

An overnight culture of the host strain SRB (P2) was infected with 10 11 of a phage eluate in SM buffer such that the culture initially grew densely but then lysed after about 6–8 h. Cell remnants were separated off from the lysed culture by centrifuging it twice at 9,000 g for 10 min. Subsequently, the phage were pelleted by centrifugation (35,000 g, 1 h), and then taken up in 700 μl of 10 mM $MgSO_4$ and extracted with phenol until a protein interface could no longer be seen. The phage DNA was then precipitated and cleaved with the restriction enzyme EcoRI, and the resulting EcoRI fragments were subcloned into the vector Bluescript, $KS^-$ (Stratagene, No.: 212208). In all, 4 clones were obtained:

| Plasmid | Beginning[1] | End[1] |
|---|---|---|
| pSP1 | 1 | 1785 |
| pSP2 | 1786 | 5833 |
| pSP3 | 5834 | 7415 |
| pSP4 | 7660 | 9793 |

[1]refers to the total sequence below

The missing section between bases 7416 and 7659 was obtained by PCR using the primers 157 (CCA TAA TAT TCA GCA GAA CTA G) (SEQ ID NO:64) and 226 (GCT GAT TCT GTA TAA GGG) (SEQ ID NO:65). The phage DNA of the clone was used as the DNA template. The conditions for the PCR were: 1.) initial denaturation: 94° C., 3 min, 2.) amplification: 1.5 min 94° C., 1 min 56° C. and 1 min 72° C. for 30 cycles.

The DNA was sequenced as described in Example 4. Both the strand and the antistrand of the total genome were sequenced. In the case of each site for EcoRI cleavage, PCR employing phage DNA of the clone as the DNA template was used to verify that there was indeed only the one EcoRI cleavage site at each subclone transition point.

TABLE 5

The position of the genes for the virus proteins GAG, POL and ENV in the full sequence of MVP-5180

| Gene | Start[1] | Stop[1] |
|---|---|---|
| GAG | 817 | 2310 |
| POL | 2073 | 5153 |
| ENV | 6260 | 8887 |

[1]The numbers give the positions of the bases in the full sequence of MVP-5180/91 (SEQ ID NO:56) The full sequence of MVP-5180/91 is presented in FIG. 4 (SEQ ID NO:56).

EXAMPLE 10

Delimitation of the full sequence of MVP-5180/91 (SEQ ID NO:56) from other HIV-1 isolates The databanks Genbank, Release 75 of 2.93, EMBL 33 of 12.92, and Swissprot 24 of 1.93 provided the basis for the following sequence comparisons. Comparisons of homology were carried out using the GCG software (version 7.2, 10.92. from the Genetics Computer Group, Wisconsin).

Initially, the sequences of GAG, POL and ENV were compared with the database at the amino acid level using the "Wordsearch" program. The 50 best homologs were in each case compared with each other using the "Pileup" program. From this, it clearly emerges that MVP-5180/91 (SEQ ID NO:56) belongs in the HIV-1 genealogical tree but branches off from it at a very early stage, even prior to the chimpanzee virus SIVcpz, and thus represents a novel HIV-1 subfamily. In order to obtain numerical values for the homologies, MVP-5180 (SEQ ID NO:56) was compared with the HIV-1, HIV-2 and SIV sequences which in each case showed the best fit, and in addition with the SIVcpz sequence, using the "Gap" program.

TABLE 6

Homology values for the amino acid sequences of GAG, POL and ENV of the MVP-5180/91 isolate

| | | | | | | | | |
|---|---|---|---|---|---|---|---|---|
| GAG | SIVcpz | 70.2% | HIV1u[2] | 69.9% | HIV2d[3] | 53.6% | SIV1a[4] | 55.1% |
| | | 83.6% | | 81.2% | | 71.3% | | 71.3% |
| POL | SIVcpz | 78.0% | HIV1u[2] | 76.1% | HIV2d[3] | 57.2% | SIVgb[5] | 57.7% |
| | | 88.0% | | 86.8% | | 71.9% | | 74.6% |
| ENV | SIVcpz | 53.4% | HIV1h[1] | 50.9% | HIV2d[3] | 34.4% | SIVat[6] | 34.4% |
| | | 67.1% | | 67.2% | | 58.7% | | 57.8% |

[1]h = hz321/Zaire,
[2]u = u455/Uganda,
[3]d = jrcst,
[4]a = agm155,
[5]gb = gb1,
[6]at = agm The upper numerical value expresses the identity and the lower value the similarity of the two sequences.

In addition to this, the database was searched at the nucleotide level using "Wordsearch" and "Gap". The homology values for the best matches in each- case are compiled in Table 7.

TABLE 7

Homology values for the nucleotide sequence of MVP-5180/91

| | HIV1 | | HIV2 | |
|---|---|---|---|---|
| gag | HIVelicg | 70.24% | HIV2bihz | 60.0% |
| pol | HIVmal | 75.0% | HIV2cam2 | 62.9% |
| env | HIVsimi84 | 59.7% | HIV2gha | 49.8 |

EXAMPLE 11

Description of the PCR amplification, cloning and sequencing of the gag gene of the HIV 5180 isolate.

In order to depict the spontaneous mutations arising during the course of virus multiplication, a part of the viral genome was cloned using the PCR technique and the DNA sequence thus obtained was compared with the sequence according to FIG. 4 (SEQ ID NO:56).

Figure 5:
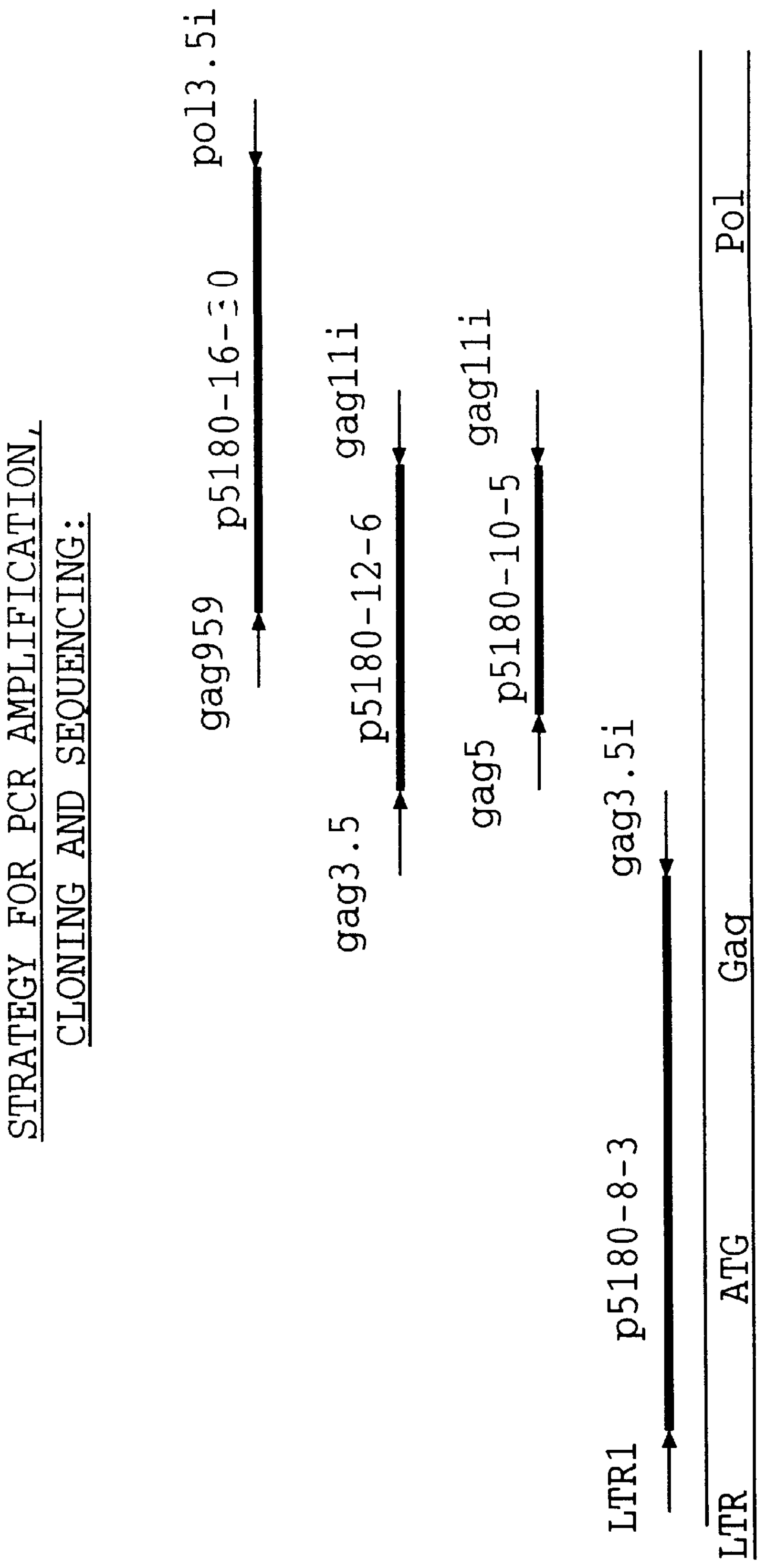
FIG. 5 depicts the strategy for PCR amplification, cloning, and sequencing of MVP-5180/91.

The gag sequence was cloned in an overlapping manner from the LTR (long terminal repeat, LTRl primer) of the left end of the MVP-5180 genome through into the pol gene (polymerase gene, pol3.5i primer). The cloning strategy is depicted schematically in FIG. 5.

The PCR reactions were carried out using the DNA primers given below, whose sequences were derived from the HIV-1 consensus sequence. The sequencings were carried out using the dideoxy chain termination method.

The sequence encoding the MVP-5180 gag gene extends from nucleotide 817 (A of the ATG start codon) to nucleotide 2300 (A of the last codon).

LTR1 (SEQ ID NO:47): 5'-CTA GCA GTG GCG CCC GAA CAG G-3' gag3.5 (SEQ ID NO:48): 5'-AAT GAG GAA GCU GCA GAU TGG GA-3' (U=A/T)

gag 3.5i (SEQ ID NO:49): 5'-TCC CAU TCT GCU GCT TCC TCA TT-3' (U=A/T)

gag5 (SEQ ID NO:50): 5'-CCA AGG GGA AGT GAC ATA GCA GGA AC-3' gag959 (SEQ ID NO:51): 5'-CGT TGT TCA GAA TTC AAA CCC-3' gag11i (SEQ ID NO:52): 5'-TCC CTA AAA AAT TAG CCT GTC-3' po13.5i (SEQ ID NO:53): 540-AAA CCT CCA ATT CCC CCT A-3'

The DNA sequence obtained using the PCR technique was compared with the DNA sequence presented in FIG. 4 (SEQ ID NO:56). A comparison of the two DNA sequences is presented in FIG. 6. FIG. 6 includes SEQ ID NO:57, which corresponds to FIG. 4 (SEQ ID NO:56) and SEQ ID NO:58, which corresponds to the DNA sequence obtained using the PCR technique. This showed that about 2% of the nucleotides differ from each other, although the virus is the same in the two cases. In FIG. 6, the upper line in each case represents the DNA sequence which is presented in FIG. 4 (SEQ ID NO:56) and the lower line represents the DNA sequence obtained using the PCR technique.

In addition, the amino acid sequence of the gag protein, elucidated using the PCR technique, was compared with the amino acid sequence of the corresponding protein deduced from FIG. 4 (SEQ ID NO:59). This showed an amino acid difference of about 2.2%. The comparison is presented in FIG. 7, the lower line in each case representing the amino acid sequence which was deduced from the sequence obtained using the PCR technique. FIG. 7 includes amino acid SEQ ID NO:59, which was elucidated in accordance with FIG. 4 (SEQ ID NO:56), and the amino acid sequence (SEQ ID NO:60) derived using the PCR technique.

EXAMPLE 12

The sequence of the virus MVP-5180 (SEQ ID NO:56) according to the invention was compared with the consensus sequences of HIV-1 and HIV-2, and with the sequence of ANT-70 (WO 89/12094), insofar as this was known.

In this connection, the following results were obtained:

TABLE 8

| Gene locus | Deviating nucleotides | Number of the nucleotides | % homology (approximated) | |
|---|---|---|---|---|
| LTR | 207 | 630 | HIV-1 | 67% |
| | 308 | | HIV-2 | 51% |
| | 115 | | ANT 70 | 82% |
| GAG | 448 | 1501 | HIV-1 | 70% |
| | 570 | | HIV-2 | 62% |
| POL | 763 | 3010 | HIV-1 | 74% |
| | 1011 | | HIV-2 | 66% |
| VIF | 183 | 578 | HIV-1 | 68% |
| | 338 | | HIV-2 | 42% |
| ENV | 1196 | 2534 | HIV-1 | 53% |
| | 1289 | | HIV-2 | 49% |
| NEF | 285 | 621 | HIV-1 | 54% |
| | 342 | | HIV-2 | 45% |
| total | 3082 | 8874 | HIV-1 | 65% |
| | 3858 | | HIV-2 | 56% |

In the above table, "HIV-1" denotes consensus sequences of the HIV-1 viruses; "HIV-2" denotes consensus sequences of HIV-2 viruses; ANT-70 denotes the partial sequence of a virus designated HIV-3 and disclosed in WO 89/12094.

The present invention therefore relates to viruses, DNA sequences and amino acid sequences, and constituent sequences thereof, which possess such a degree of homology with the sequence presented in FIG. 4 (SEQ ID NO:56), based on the gene loci, that at most the fractions given in Table 9, expressed in % values, are different.

TABLE 9

| | Homology based on gene loci, expressed as maximum differences | | |
|---|---|---|---|
| Gene locus | Differences | Preferred differences | Particularly preferred differences |
| LTR | 17% | 15% | 10% |
| GAG | 29% | 28% | 14% |
| POL | 25% | 24% | 12% |
| VIF | 31% | 30% | 15% |
| ENV | 46% | 45% | 22% |
| NEF | 16% | 12% | 10% |

The homology values in % given in Table 9 mean that, when comparing the sequence according to FIG. 4 (SEQ ID NO:56) with a sequence of another virus, at most a fraction of the sequence corresponding to the abovementioned percentage values may be different.

EXAMPLE 13

V3 Loop

Figure 8:
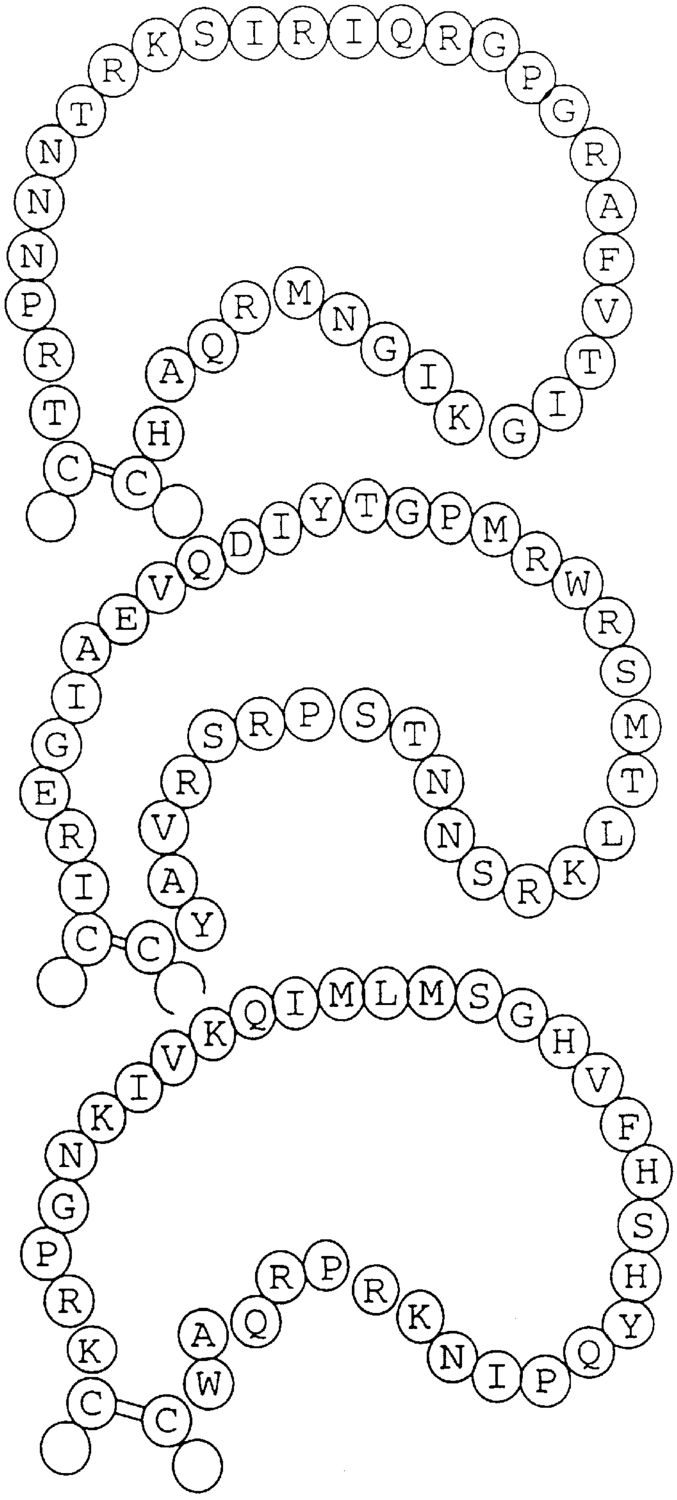
FIG. 8 depicts the immunological specificities of the V3 loop of HIV-1, HIV-2, and MVP-5180/91.

This loop is the main neutralizing region in HIV and the immunological specificities of the region are documented in summary form in FIG. 8. This is a copy from a work by Peter Nara (1990) from AIDS. The amino acid sequence of the V3 loop is shown diagrammatically and is compared with the IIIB virus, now LAI, and the first HIV-2 isolate (ROD). Individual amino acids are conserved at the cystine bridge. Whereas the crown of HIV-1 is GPGR or GPGQ and that of HIV-2 is GHVF, the crown of MVP-5180/91 (SEQ ID NO:56) is formed from the amino acids GPMR. The motif with methionine has not previously been described and, emphasizes the individuality of MVP-5180/91 (SEQ ID NO:56).

After having determined the nucleotide sequence of the virus the V3-loop-region was amplified using the PCR-technique by using suitable primers. Some mutations have been observed, especially a change of the methionine codon (ATG) to the leucine codon (CTG).

In the following the amino acid sequence derived from the cloned nucleic acid is compared with a sequence obtained after amplification with the help of PCR technology.

MvP 5180 (cloned) (SEQ ID NO:54): CIREGIAEVQDIYTGPM-RWRSMTLKRSNNTSPRSRVAYC

MvP 5180 (PCT technique) (SEQ ID NO:55): CIREGIAE-VQDLHTGPLRWRSMTLKKSSNSHTQPRSKVAYC

EXAMPLE 14

In order to demonstrate that even those sera which cannot be identified in a normal HIV-1+2 screening test can be proved to be HIV-1-positive with the aid of the virus MVP-5180 (SEQ ID NO:56) according to the invention, or antigens derived therefrom, various sera from patients from the Cameroons were examined in the EIA test.

156 anti-HIV-1-positive sera were examined in a study carried out in the Cameroons. Substantial, diagnostically relevant differences were observed in two of these sera. The extinctions which were measured are given in Table 10 below. CAM-A and CAM-B denote the sera of different patients.

TABLE 10

| Patient sera | MVP-5180-EIA | HIV-1 + HIV-2 EIA |
|---|---|---|
| CAM-A | 2.886 | 1.623 |
| CAM-B | 1.102 | 0.386 |

The cutoff for both tests was 0.300.

In a further study on 47 anti-HIV-1-positive sera from the Cameroons, two sera were of particular note. One of these (93-1000) derives from a patient showing relatively few symptoms and the other (93-1001) from a patient suffering from AIDS. The extinction values for the two EIA tests are compared in Table 11 below:

TABLE 11

| Patient sera | MVP-5180-EIA | HIV-1 + HIV-2 EIA |
|---|---|---|
| 93–1000 | >2.5 | 1.495 |
| 93–1001 | 0.692 | 0.314 |

The cutoff was 0.3 in this case as well. The extinction values for patient 93-1001 demonstrate that the normal HIV-1+ HIV-2 EIA can fail whereas clear detection is possible the antigen according to the invention is employed.

What is claimed is:

1. Virus MvP-5180/91, deposited with the European Collection of Animal Cell Culture (ECACC) under No. V 920 92 318.

2. A variant virus, which is a variant of virus MvP-5180/91, wherein said variant has a genome that has a nucleotide sequence that shows at least 66% homology to SEQ ID NO:37 or SEQ ID NO:38.

3. The variant virus of claim 2, wherein said variant has a genome that has a nucleotide sequence that shows at least 75% homology to SEQ ID NO:37 or SEQ ID NO:38.

4. The variant virus of claim 2, wherein said variant has a genome that has a nucleotide sequence that shows at least 85% homology to SEQ ID NO:37 or SEQ ID NO:38.

5. A variant virus, which is a variant of virus MvP-5180/91, wherein said variant has a genome that has a nucleotide sequence that shows at least 66% homology to SEQ ID NO:44 or SEQ ID NO:45.

6. The variant virus of claim 5, wherein said variant has a genome that has a nucleotide sequence that shows at least 75% homology to SEQ ID NO:44 or SEQ ID NO:45.

7. The variant virus of claim 5, wherein said variant has a genome that has a nucleotide sequence that shows at least 85% homology to SEQ ID NO:44 or SEQ ID NO:45.

8. The variant virus of claim 5, wherein said variant has a genome that has a sequence that shows at least 66% homology to SEQ ID NO:44 or SEQ ID NO:45 over at least 50 nucleotides.

9. The variant virus of claim 8, wherein said variant has a genome that has a sequence that shows at least 66% homology to SEQ ID NO:44 or SEQ ID NO:45 over at least 100 nucleotides.

10. The variant virus of claim 5, wherein said variant has a genome that has a sequence that shows at least 75% homology to SEQ ID NO:44 or SEQ ID NO:45 over at least 50 nucleotides.

11. The variant virus of claim 10, wherein said variant has a genome that has a sequence that shows at least 75% homology to SEQ ID NO:44 or SEQ ID NO:45 over at least 100 nucleotides.

12. The variant virus of claim 5, wherein said variant has a genome that has a sequence that shows at least 85% homology to SEQ ID NO:44 or SEQ ID NO:45 over at least 50 nucleotides.

13. The variant virus of claim 12, wherein said variant has a genome that has a sequence that shows at least 85% homology to SEQ ID NO:44 or SEQ ID NO:45 over at least 100 nucleotides.

14. A variant virus, which is a variant of virus MvP-5180/91, wherein said variant has a genome that encodes a polypeptide that shows at least 66% homology to SEQ ID NO:39.

15. The variant virus of claim 14, wherein said variant has a genome that has a sequence that encodes a polypeptide that shows at least 75% homology to SEQ ID NO:39.

16. The variant virus of claim 14, wherein said variant has a genome that encodes a polypeptide that shows at least 85% homology to SEQ ID NO:39.

17. A variant virus, which is a variant of virus MvP-5180/91, wherein said variant has a genome that encodes a polypeptide that shows at least 66% homology to SEQ ID NO:46.

18. The variant virus of claim 17, wherein said variant has a genome that encodes a polypeptide that shows at least 66% homology to SEQ ID NO:46 over at least 16 amino acid residues.

19. The variant virus of claim 18, wherein said variant has a genome that encodes a polypeptide that shows at least 66% homology to SEQ ID NO:46 over at least 33 amino acid residues.

20. A variant virus, which is a variant of virus MvP-5180/91, wherein said variant has a genome that encodes a polypeptide that shows at least 75% homology to SEQ ID NO:46.

21. The variant virus of claim 20, wherein said variant has a genome that encodes a polypeptide that shows at least 75% homology to SEQ ID NO:46 over at least 16 amino acid residues.

22. The variant virus of claim 21, wherein said variant has a genome that encodes a polypeptide that shows at least 75% homology to SEQ ID NO:46 over at least 33 amino acid residues.

23. A variant virus, which is a variant of virus MvP-5180/91, wherein said variant has a genome that encodes a polypeptide that shows at least 85% homology to SEQ ID NO:46.

24. The variant virus of claim 23, wherein said variant has a genome that encodes a polypeptide that shows at least 85% homology to SEQ ID NO:46 over at least 16 amino acid residues.

25. The variant virus of claim 24, wherein said variant has a genome that encodes a polypeptide that shows at least 85% homology to SEQ ID NO:46 over at least 33 amino acid residues.

26. The virus of claim 2, wherein said virus has a reverse transcriptase that is magnesium dependent, but not manganese dependent.

27. A variant virus, which is a variant of virus MvP-5180/91, wherein said variant has a genome that has a nucleotide sequence that shows at least 98% homology to SEQ ID NO:57.

28. A variant virus, which is a variant of virus MvP-5180/91, wherein said variant has a genome that encodes a polypeptide that shows at least 97.8% homology to SEQ ID NO:59.

29. A variant virus, which is a variant of virus MvP-5180/91, wherein said variant has a genome that encodes a polypeptide that shows at least 77.8% homology to SEQ ID NO:54.

30. A variant virus, which is a variant of virus MvP-5180/91, wherein said variant has an LTR that shows at least 83% homology to the long terminal repeat (LTR) of virus MvP-5180/91.

31. The variant virus of claim 30, wherein said variant LTR shows at least 85% homology to the LTR of virus MvP-5180/91.

32. The variant virus of claim 30, wherein said variant LTR shows at least 90% homology to the LTR of virus MvP-5180/91.

33. A variant virus, which is a variant of virus MvP-5180/91, wherein said variant has a GAG gene that shows at least 71% homology to the GAG gene of virus MvP-5180/91.

34. The variant virus of claim 33, wherein said variant LTR shows at least 72% homology to the GAG gene of virus MvP-5180/91.

35. The variant virus of claim 33, wherein said variant LTR shows at least 86% homology to the LTR of virus MvP-5180/91.

36. A variant virus, which is a variant of virus MvP-5180/91, wherein said variant has a POL gene that shows at least 75% homology to the POL gene of virus MvP-5180/91.

37. The variant virus of claim 36, wherein said variant POL gene shows at least 86% homology to the POL gene of virus MvP-5180/91.

38. The variant virus of claim 36, wherein said variant POL gene shows at least 88% homology to the POL gene of virus MvP-5180/91.

39. A variant virus, which is a variant of virus MvP-5180/91, wherein said variant has a VIF gene that shows at least 68% homology to the VIF gene of virus MvP-5180/91.

40. The variant virus of claim 39, wherein said variant VIF gene shows at least 70% homology to the VIF gene of virus MvP-5180/91.

41. The variant virus of claim 39, wherein said variant VIF gene shows at least 85% homology to the VIF gene of virus MvP-5180/91.

42. A variant virus, which is a variant of virus MvP-5180/91, wherein said variant has an ENV gene that shows at least 54% homology to the ENV gene of virus MvP-5180/91.

43. The variant virus of claim 42, wherein said variant ENV gene shows at least 55% homology to the ENV gene of virus MvP-5180/91.

44. The variant virus of claim 42, wherein said variant ENV gene shows at least 88% homology to the ENV gene of virus MvP-5180/91.

45. A variant virus, which is a variant of virus MvP-5180/91, wherein said variant has an NEF gene that shows at least 55% homology to the NEF gene of virus MvP-5180/91.

46. The variant virus of claim 45, wherein said variant NEF gene shows at least 84% homology to the NEF gene of virus MvP-5180/91.

47. The variant virus of claim 45, wherein said variant NEF gene shows at least 88% homology to the NEF gene of virus MvP-5180/91.

48. The variant virus of claim 45, wherein said variant NEF gene shows at least 90% homology to the NEF gene of virus MvP-5180/91.

* * * * *

SEQUENCE LISTING

<160> NUMBER OF SEQ ID NOS: 67

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 1
ctactagtac ccttcagg 18

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 2
cggtctacat agtctctaaa g 21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 3
ccacctatcc cagtaggaga a 21

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 4
cctttggtcc ttgtcttatg tccagaatgc 30

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 5
tgggaagttc aattaggaat accac 25

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 6
cctacataga aatcatccat gtattg 26

<210> SEQ ID NO 7
<211> LENGTH: 19

-continued

<212> TYPE: DNA
<213> ORGANISM: Artificial Sequence
<220> FEATURE:
<223> OTHER INFORMATION: Description of Artificial Sequence: primer

<400> SEQUENCE: 7
tggatgtggg tgatgcata 19

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 8
agcacattgt actgatatct a 21

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 9
agtgggggga catcaagcag cc 22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 10
tgctatgtca cttccccttg gt 22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 11
ccatgcaaat gttaaaagag ac 22

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 12
ggcctggtgc aataggccc 19

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 13

-continued gtgcttccac agggatggaa 20

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 14
atcatccatg tattgata 18

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 15
aatggagcca gtagatccta 20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 16
tgtctccgct tcttcctgcc 20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 17
gagccctgga agcatccagg 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 18
ggagatgcct aaggcttttg 20

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 19
tgttccttgg gttcttg 17

<210> SEQ ID NO 20
<211> LENGTH: 20
<212> TYPE: DNA
<213> ORGANISM: Artificial Sequence -continued
<220> FEATURE:
<223> OTHER INFORMATION: Description of Artificial Sequence: primer

<400> SEQUENCE: 20
gagttttcca gagcaacccc 20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 21
agcagcagga agcactatgg 20

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 22
gccccagact gtgagttgca acag 24

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 23
gcacagtaca atgtacacat gg 22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 24
cagtagaaaa attcccctcc ac 22

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 25
tcaggatcca tgggcagtct agcagaagaa g 31

<210> SEQ ID NO 26
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 26
atgctcgaga actgcagcat cgattctggg tcccctcctg ag 42

-continued

<210> SEQ ID NO 27
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 27
cgagaactgc agcatcgatg ctgctcccaa gaacccaagg 40

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 28
ggagctgctt gatgccccag a 21

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 29
tgatgacagc atgtcaggga gt 22

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 30
gctgacattt atcacagctg gctac 25

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 31
tatcacctag aactttaaat gcatggg 27

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 32
agtccctgac atgctgtcat ca 22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: primer -continued

<400> SEQUENCE: 33
gtggagggga atttttctac tg 22

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 34
cctgctgctc ccaagaaccc aagg 24

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 35
agcagcagga agcactatgg 20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 36
gagttttcca gagcaacccc 20

<210> SEQ ID NO 37
<211> LENGTH: 195
<212> TYPE: DNA
<213> ORGANISM: Human immunodeficiency virus
<220> FEATURE:
<221> NAME/KEY: CDS
<222> LOCATION: (3)..(194)

<400> SEQUENCE: 37

```
gc gca gcg gca aca gcg ctg acg gta cgg acc cac agt gta ctg aag        47
   Ala Ala Ala Thr Ala Leu Thr Val Arg Thr His Ser Val Leu Lys
     1               5                  10                  15

ggt ata gtg caa cag cag gac aac ctg ctg aga gcg ata cag gcc cag       95
Gly Ile Val Gln Gln Gln Asp Asn Leu Leu Arg Ala Ile Gln Ala Gln
                20                  25                  30

caa cac ttg ctg agg tta tct gta tgg ggt att aga caa ctc cga gct      143
Gln His Leu Leu Arg Leu Ser Val Trp Gly Ile Arg Gln Leu Arg Ala
            35                  40                  45

cgc ctg caa gcc tta gaa acc ctt ata cag aat cag caa cgc cta aac      191
Arg Leu Gln Ala Leu Glu Thr Leu Ile Gln Asn Gln Gln Arg Leu Asn
        50                  55                  60

cta t                                                                195
Leu
```

<210> SEQ ID NO 38
<211> LENGTH: 195
<212> TYPE: DNA
<213> ORGANISM: Human immunodeficiency virus

<400> SEQUENCE: 38

-continued

```
ataggtttag gcgttgctga ttctgtataa gggtttctaa ggcttgcagg cgagctcgga      60

gttgtctaat accccataca gataacctca gcaagtgttg ctgggcctgt atcgctctca     120

gcaggttgtc ctgctgttgc actataccct tcagtacact gtgggtccgt accgtcagcg     180

ctgttgccgc tgcgc                                                      195
```

```
<210> SEQ ID NO 39
<211> LENGTH: 64
<212> TYPE: PRT
<213> ORGANISM: Human immunodeficiency virus

<400> SEQUENCE: 39

Ala Ala Ala Thr Ala Leu Thr Val Arg Thr His Ser Val Leu Lys Gly
  1               5                  10                  15

Ile Val Gln Gln Gln Asp Asn Leu Leu Arg Ala Ile Gln Ala Gln Gln
             20                  25                  30

His Leu Leu Arg Leu Ser Val Trp Gly Ile Arg Gln Leu Arg Ala Arg
         35                  40                  45

Leu Gln Ala Leu Glu Thr Leu Ile Gln Asn Gln Gln Arg Leu Asn Leu
     50                  55                  60
```

```
<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 40

cagaatcagc aacgcctaaa cc                                               22
```

```
<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 41

gccctgtctt attcttctag g                                                21
```

```
<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 42

gcctgcaagc cttagaaacc                                                  20
```

```
<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 43

gcactatacc cttcagtaca ctg                                              23
```

```
<210> SEQ ID NO 44
<211> LENGTH: 1057
```

-continued

<212> TYPE: DNA
<213> ORGANISM: Human immunodeficiency virus
<220> FEATURE:
<221> NAME/KEY: CDS
<222> LOCATION: (3)..(1055)

<400> SEQUENCE: 44 aa atg tca aga cca ata ata aac att cac acc cct cac agg gaa aaa 47
Met Ser Arg Pro Ile Ile Asn Ile His Thr Pro His Arg Glu Lys
1 5 10 15 aga cga gta gga ttg gga atg cta ttc ttg ggg gtg cta agt gca gca 95
Arg Arg Val Gly Leu Gly Met Leu Phe Leu Gly Val Leu Ser Ala Ala
20 25 30 ggt agc act atg ggc gca gcg gca aca gcg ctg acg gta cgg acc cac 143
Gly Ser Thr Met Gly Ala Ala Ala Thr Ala Leu Thr Val Arg Thr His
35 40 45 agt gta ctg aag ggt ata gtg caa cag cag gac aac ctg ctg aga gcg 191
Ser Val Leu Lys Gly Ile Val Gln Gln Gln Asp Asn Leu Leu Arg Ala
50 55 60 ata cag gcc cag caa cac ttg ctg agg tta tct gta tgg ggt att aga 239
Ile Gln Ala Gln Gln His Leu Leu Arg Leu Ser Val Trp Gly Ile Arg
65 70 75 caa ctc cga gct cgc ctg caa gcc tta gaa acc ctt ata cag aat cag 287
Gln Leu Arg Ala Arg Leu Gln Ala Leu Glu Thr Leu Ile Gln Asn Gln
80 85 90 95 caa cgc cta aac cta tgg ggc tgt aaa gga aaa cta atc tgt tac aca 335
Gln Arg Leu Asn Leu Trp Gly Cys Lys Gly Lys Leu Ile Cys Tyr Thr
100 105 110 tca gta aaa tgg aac aca tca tgg tca gga gga tat aat gat gac agt 383
Ser Val Lys Trp Asn Thr Ser Trp Ser Gly Gly Tyr Asn Asp Asp Ser
115 120 125 att tgg gac aac ctt aca tgg cag caa tgg gac caa cac ata aac aat 431
Ile Trp Asp Asn Leu Thr Trp Gln Gln Trp Asp Gln His Ile Asn Asn
130 135 140 gta agc tcc att ata tat gat gaa ata caa gca gca caa gac caa cag 479
Val Ser Ser Ile Ile Tyr Asp Glu Ile Gln Ala Ala Gln Asp Gln Gln
145 150 155 gaa aag aat gta aaa gca ttg ttg gag cta gat gaa tgg gcc tct ctt 527
Glu Lys Asn Val Lys Ala Leu Leu Glu Leu Asp Glu Trp Ala Ser Leu
160 165 170 175 tgg aat tgg ttt gac ata act aaa tgg ttg tgg tat ata aaa ata gct 575
Trp Asn Trp Phe Asp Ile Thr Lys Trp Leu Trp Tyr Ile Lys Ile Ala
180 185 190 ata atc ata gtg gga gca cta ata ggt ata aga gtt atc atg ata gta 623
Ile Ile Ile Val Gly Ala Leu Ile Gly Ile Arg Val Ile Met Ile Val
195 200 205 ctt aat cta gtg aag aac att agg cag gga tat caa ccc ctc tcg ttg 671
Leu Asn Leu Val Lys Asn Ile Arg Gln Gly Tyr Gln Pro Leu Ser Leu
210 215 220 cag atc cct gtc cca cac cgg cag gaa gca gaa acg cca gga aga aca 719
Gln Ile Pro Val Pro His Arg Gln Glu Ala Glu Thr Pro Gly Arg Thr
225 230 235 gga gaa gaa ggt gga gaa gga gac agg ccc aag tgg aca gcc ttg cca 767
Gly Glu Glu Gly Gly Glu Gly Asp Arg Pro Lys Trp Thr Ala Leu Pro
240 245 250 255 cca gga ttc ttg caa cag ttg tac acg gat ctc agg aca ata atc ttg 815
Pro Gly Phe Leu Gln Gln Leu Tyr Thr Asp Leu Arg Thr Ile Ile Leu
260 265 270 tgg act tac cac ctc ttg agc aac tta ata tca ggg atc cgg agg ctg 863
Trp Thr Tyr His Leu Leu Ser Asn Leu Ile Ser Gly Ile Arg Arg Leu
275 280 285

-continued

```
atc gac tac ctg gga ctg gga ctg tgg atc ctg gga caa aag aca att      911
Ile Asp Tyr Leu Gly Leu Gly Leu Trp Ile Leu Gly Gln Lys Thr Ile
        290                 295                 300

gaa gct tgt aga ctt tgt gga gct gta atg caa tat tgg cta caa gaa      959
Glu Ala Cys Arg Leu Cys Gly Ala Val Met Gln Tyr Trp Leu Gln Glu
    305                 310                 315

ttg aaa aat agt gct aca aac ctg ctt gat act att gca gtg tca gtt     1007
Leu Lys Asn Ser Ala Thr Asn Leu Leu Asp Thr Ile Ala Val Ser Val
320                 325                 330                 335

gcc aat tgg act gac ggc atc atc tta ggt cta caa aga ata gga caa     1055
Ala Asn Trp Thr Asp Gly Ile Ile Leu Gly Leu Gln Arg Ile Gly Gln
                340                 345                 350

gg                                                                  1057


<210> SEQ ID NO 45
<211> LENGTH: 1057
<212> TYPE: DNA
<213> ORGANISM: Human immunodeficiency virus

<400> SEQUENCE: 45

ccttgtccta ttctttgtag acctaagatg atgccgtcag tccaattggc aactgcaact     60

gcaatagtat caagcaggtt tgtagcacta tttttcaatt cttgtagcca atattgcatt    120

acagctccac aaagtctaca agcttcaatt gtcttttgtc ccaggatcca cagtcccagt    180

cccaggtagt cgatcagcct ccggatccct gatattaagt tgctcaagag gtggtaagtc    240

cacaagatta ttgtcctgag atccgtgtac aactgttgca agaatcctgg tggcaaggct    300

gtccacttgg gcctgtctcc ttctccacct tcttctcctg ttcttcctgg cgtttctgct    360

tcctgccggt gtgggacagg gatctgcaac gagaggggtt gatatccctg cctaatgttc    420

ttcactagat taagtactat catgataact cttataccta ttagtgctcc cactatgatt    480

atagctattt ttatatacca caaccattta gttatgtcaa accaattcca aagagaggcc    540

cattcatcta gctccaacaa tgcttttaca ttcttttcct gttggtcttg tgctgcttgt    600

atttcatcat atataatgga gcttacattg tttatgtgtt ggtcccattg ctgccatgta    660

aggttgtccc aaatactgtc atcattatat cctcctgacc atgatgtgtt ccattttact    720

gatgtgtaac agattagttt tcctttacag ccccataggt ttaggcgttg ctgattctgt    780

ataagggttt ctaaggcttg caggcgagct cggagttgtc taatacccca tacagataac    840

ctcagcaagt gttgctgggc ctgtatcgct ctcagcaggt tgtcctgctg ttgcactata    900

cccttcagta cactgtgggt ccgtaccgtc agcgctgttg ccgctgcgcc catagtgcta    960

cctgctgcac ttagcacccc caagaatagc attcccaatc ctactgctct tttttccctg   1020

tgaggggtgt gaatgtttat tattggtctt gacattt                            1057


<210> SEQ ID NO 46
<211> LENGTH: 351
<212> TYPE: PRT
<213> ORGANISM: Human immunodeficiency virus

<400> SEQUENCE: 46

Met Ser Arg Pro Ile Ile Asn Ile His Thr Pro His Arg Glu Lys Arg
  1               5                  10                  15

Arg Val Gly Leu Gly Met Leu Phe Leu Gly Val Leu Ser Ala Ala Gly
             20                  25                  30

Ser Thr Met Gly Ala Ala Ala Thr Ala Leu Thr Val Arg Thr His Ser
        35                  40                  45
```

-continued

```
Val Leu Lys Gly Ile Val Gln Gln Gln Asp Asn Leu Leu Arg Ala Ile
     50                  55                  60

Gln Ala Gln Gln His Leu Leu Arg Leu Ser Val Trp Gly Ile Arg Gln
 65                  70                  75                  80

Leu Arg Ala Arg Leu Gln Ala Leu Glu Thr Leu Ile Gln Asn Gln Gln
                 85                  90                  95

Arg Leu Asn Leu Trp Gly Cys Lys Gly Lys Leu Ile Cys Tyr Thr Ser
            100                 105                 110

Val Lys Trp Asn Thr Ser Trp Ser Gly Gly Tyr Asn Asp Asp Ser Ile
        115                 120                 125

Trp Asp Asn Leu Thr Trp Gln Gln Trp Asp Gln His Ile Asn Asn Val
    130                 135                 140

Ser Ser Ile Ile Tyr Asp Glu Ile Gln Ala Ala Gln Asp Gln Gln Glu
145                 150                 155                 160

Lys Asn Val Lys Ala Leu Leu Glu Leu Asp Glu Trp Ala Ser Leu Trp
                165                 170                 175

Asn Trp Phe Asp Ile Thr Lys Trp Leu Trp Tyr Ile Lys Ile Ala Ile
            180                 185                 190

Ile Ile Val Gly Ala Leu Ile Gly Ile Arg Val Ile Met Ile Val Leu
        195                 200                 205

Asn Leu Val Lys Asn Ile Arg Gln Gly Tyr Gln Pro Leu Ser Leu Gln
    210                 215                 220

Ile Pro Val Pro His Arg Gln Glu Ala Glu Thr Pro Gly Arg Thr Gly
225                 230                 235                 240

Glu Glu Gly Gly Glu Gly Asp Arg Pro Lys Trp Thr Ala Leu Pro Pro
                245                 250                 255

Gly Phe Leu Gln Gln Leu Tyr Thr Asp Leu Arg Thr Ile Ile Leu Trp
            260                 265                 270

Thr Tyr His Leu Leu Ser Asn Leu Ile Ser Gly Ile Arg Arg Leu Ile
        275                 280                 285

Asp Tyr Leu Gly Leu Gly Leu Trp Ile Leu Gly Gln Lys Thr Ile Glu
    290                 295                 300

Ala Cys Arg Leu Cys Gly Ala Val Met Gln Tyr Trp Leu Gln Glu Leu
305                 310                 315                 320

Lys Asn Ser Ala Thr Asn Leu Leu Asp Thr Ile Ala Val Ser Val Ala
                325                 330                 335

Asn Trp Thr Asp Gly Ile Ile Leu Gly Leu Gln Arg Ile Gly Gln
            340                 345                 350
```

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 47
ctagcagtgg cgcccgaaca gg 22

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 48

-continued aatgaggaag cwgcagawtg gga 23

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 49
tcccawtctg cwgcttcctc att 23

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 50
ccaaggggaa gtgacatagc aggaac 26

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 51
cgttgttcag aattcaaacc c 21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 52
tccctaaaaa attagcctgt c 21

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 53
aaacctccaa ttcccccta 19

<210> SEQ ID NO 54
<211> LENGTH: 39
<212> TYPE: PRT
<213> ORGANISM: Human immunodeficiency virus

<400> SEQUENCE: 54

```
Cys Ile Arg Glu Gly Ile Ala Glu Val Gln Asp Ile Tyr Thr Gly Pro
  1               5                  10                  15

Met Arg Trp Arg Ser Met Thr Leu Lys Arg Ser Asn Asn Thr Ser Pro
             20                  25                  30

Arg Ser Arg Val Ala Tyr Cys
         35
```

-continued

<210> SEQ ID NO 55
<211> LENGTH: 41
<212> TYPE: PRT
<213> ORGANISM: Human immunodeficiency virus

<400> SEQUENCE: 55

Cys Ile Arg Glu Gly Ile Ala Glu Val Gln Asp Leu His Thr Gly Pro
1 5 10 15

Leu Arg Trp Arg Ser Met Thr Leu Lys Lys Ser Ser Asn Ser His Thr
20 25 30

Gln Pro Arg Ser Lys Val Ala Tyr Cys
35 40

<210> SEQ ID NO 56
<211> LENGTH: 9793
<212> TYPE: DNA
<213> ORGANISM: Human immunodeficiency virus

<400> SEQUENCE: 56
ctggatgggt taatttactc ccataagaga gcagaaatcc tggatctctg gatatatcac 60
actcagggat tcttccctga ttggcagtgt tacacaccgg gaccaggacc tagattccca 120
ctgacatttg gatggttgtt taaactggta ccagtgtcag cagaagaggc agagagactg 180
ggtaatacaa atgaagatgc tagtcttcta catccagctt gtaatcatgg agctgaggat 240
gcacacgggg agatactaaa atggcagttt gatagatcat taggcttaac acatatagcc 300
ctgcaaaagc acccagagct cttccccaag taactgacac tgcgggactt tccagactgc 360
tgacactgcg gggactttcc agcgtgggag ggataagggg cggttcgggg agtggctaac 420
cctcagatgc tgcatataag cagctgcttt ccgcttgtac cgggtcttag ttagaggacc 480
aggtctgagc ccgggagctc cctggcctct agctgaaccc gctgcttaac gctcaataaa 540
gcttgccttg agtgagaagc agtgtgtgct catctgttca accctggtgt ctagagatcc 600
ctcagatcac ttagactgaa gcagaaaatc tctagcagtg gcgcccgaac agggacgcga 660
aagtgaaagt ggaaccaggg aagaaaacct ccgacgcaac gggctcggct tagcggagtg 720
cacctgctaa gaggcgagag gaactcacaa gagggtgagt aaatttgctg gcggtggcca 780
gacctagggg aagggcgaag tccctagggg aggaagatgg gtgcgagagc gtctgtgttg 840
acagggagta aattggatgc atgggaacga attaggttaa ggccaggatc taaaaaggca 900
tataggctaa aacatttagt atgggcaagc agggagctgg aaagatacgc atgtaatcct 960
ggtctattag aaactgcaga aggtactgag caactgctac agcagttaga gccagctctc 1020
aagacagggt cagaggacct gaaatctctc tggaacgcaa tagcagtact ctggtgcgtt 1080
cacaacagat ttgacatccg agatacacag caggcaatac aaaagttaaa ggaagtaatg 1140
gcaagcagga agtctgcaga ggccgctaag gaagaaacaa gccctaggca gacaagtcaa 1200
aattacccta tagtaacaaa tgcacaggga caaatggtac atcaagccat ctcccccagg 1260
actttaaatg catgggtaaa ggcagtagaa gagaaggcct ttaaccctga aattattcct 1320
atgtttatgg cattatcaga aggggctgtc ccctatgata tcaataccat gctgaatgcc 1380 ataggggggac accaaggggc tttacaagtg ttgaaggaag taatcaatga ggaagcagca 1440
gaatgggata gaactcatcc accagcaatg gggccgttac caccagggca gataagggaa 1500
ccaacaggaa gtgacattgc tggaacaact agcacacagc aagagcaaat tatatggact 1560
actagagggg ctaactctat cccagtagga gacatctata gaaaatggat agtgctagga 1620

-continued

```
ctaaacaaaa tggtaaaaat gtacagtcca gtgagcatct tagatattag gcagggacca   1680
aaagaaccat tcagagatta tgtagatcgg ttttacaaaa cattaagagc tgagcaagct   1740
actcaagaag taaagaattg gatgacagaa accttgcttg ttcagaattc aaacccagat   1800
tgtaaacaaa ttctgaaagc attaggacca gaagctactt tagaagaaat gatggtagcc   1860
tgtcaaggag taggagggcc aactcacaag gcaaaaatac tagcagaagc aatggcttct   1920
gcccagcaag atttaaaagg aggatacaca gcagtattca tgcaaagagg gcagaatcca   1980
aatagaaaag ggcccataaa atgcttcaat tgtggaaaag agggacatat agcaaaaaac   2040
tgtcgagcac ctagaaaaag ggttgctgg aaatgtggac aggaaggtca ccaaatgaaa   2100
gattgcaaaa atggaagaca ggcaaatttt ttagggaagt actggcctcc ggggggcacg   2160
aggccaggca attatgtgca gaaacaagtg tccccatcag ccccaccaat ggaggaggca   2220
gtgaaggaac aagagaatca gagtcagaag gggatcagg aagagctgta cccatttgcc   2280
tccctcaaat ccctctttgg gacagaccaa tagtcacagc aaaggttggg ggtcatctat   2340
gtgaggcttt actggataca ggggcagatg atacagtatt aaataacata caattagaag   2400
gaagatggac accaaaaatg ataggggggta taggaggctt tataaaagta aaagagtata   2460
acaatgtgac agtagaagta caaggaaagg aagtacaggg aacagtattg gtgggaccta   2520
ctcctgttaa tattcttggg agaaacatat tgacaggatt aggatgtaca ctaaatttcc   2580
ctataagtcc catagcccca gtgccagtaa agctaaaacc aggaatggat ggaccaaaag   2640
taaaacaatg gcccctatct agagagaaaa tagaagcact aactgcaata tgtcaagaaa   2700
tggaacagga aggaaaaatc tcaagaatag gacctgaaaa tccttataat acacctattt   2760
ttgctataaa aaagaaagat agcactaagt ggagaaaatt ggtagacttc agagaattaa   2820
ataaaagaac acaagatttc tgggaggtgc aattaggtat tccacatcca gggggtttaa   2880
agcaaaggca atctgttaca gtcttagatg taggagatgc ttatttctca tgccctttag   2940
atccagactt tagaaaatac actgccttca ctattcctag tgtgaacaat gagaccccag   3000
gagtaagata ccagtacaat gtcctcccgc aagggtggaa aggttcacca gccatatttc   3060
agagttcaat gacaaagatt ctagatccat ttagaaaaag caacccagaa gtagaaattt   3120
atcagtacat agatgactta tatgtaggat cagatttacc attggcagaa catagaaaga   3180
gggtcgaatt gcttagggaa catttatatc agtggggatt tactacccct gataaaaagc   3240
atcagaagga acctcccttt ttatggatgg gatatgagct ccacccagac aagtggacag   3300
tacagcccat ccaattgcct gacaaagaag tgtggacagt aaatgatata caaaaattag   3360
taggaaaatt aaattgggca agtcaaatct atcaaggaat tagagtaaaa gaattgtgca   3420
agttaatcag aggaaccaaa tcattgacag aggtagtacc tttaagtaaa gaggcagaac   3480
tagaattaga agaaaacaga gaaaagctaa aagagccagt acatggagta tattaccagc   3540
ctgacaaaga cttgtgggtt agtattcaga agcatggaga agggcaatgg acttaccagg   3600
tatatcagga tgaacataag aaccttaaaa caggaaaata tgctaggcaa aaggcctccc   3660
acacaaatga tataagacaa ttggcagaag tagtccagaa ggtgtctcaa gaagctatag   3720
ttatatgggg gaaattacct aaattcaggc tgccagttac tagagaaact tgggaaactt   3780
ggtgggcaga atattggcag gccacctgga ttcctgaatg ggaatttgtc agcacacccc   3840
cattgatcaa attatggtac cagttagaaa cagaacctat tgtaggggca gaaacctttt   3900
atgtagatgg agcagctaat aggaatacaa aactaggaaa ggcgggatat gttacagaac   3960
```

-continued

```
aaggaaaaca gaacataata aagttagaag agacaaccaa tcaaaaggct gaattaatgg   4020
ctgtattaat agccttgcag gattccaagg agcaagtaaa catagtaaca gactcacaat   4080
atgtattggg catcatatcc tcccaaccaa cacagagtga ctcccctata gttcagcaga   4140
taatagagga actaacaaaa aaggaacgag tgtatcttac atgggttcct gctcacaaag   4200
gcataggagg aaatgaaaaa atagataaat tagtaagcaa agacattaga agagtcctgt   4260
tcctggaagg aatagatcag gcacaagaag atcatgaaaa atatcatagt aattggagag   4320
cattagctag tgactttgga ttaccaccaa tagtagccaa ggaaatcatt gctagttgtc   4380
ctaaatgcca tataaaaggg gaagcaacgc atggtcaagt agactacagc ccagagatat   4440
ggcaaatgga ttgtacacat ttagaaggca aaatcataat agttgctgtc catgtagcaa   4500
gtgactttat agaagcagag gtgataccag cagaaacagg acaggaaact gcctatttcc   4560
tgttaaaatt agcagcaaga tggcctgtca aagtaataca tacagacaat ggacctaatt   4620
ttacaagtgc agccatgaaa gctgcatgtt ggtggacagg catacaacat gagtttggga   4680
taccatataa tccacaaagt caaggagtag tagaagccat gaataaagaa ttaaaatcta   4740
ttatacagca ggtgagggac caagcagagc atttaaaaac agcagtacaa atggcagtct   4800
ttgttcacaa ttttaaaaga aaagggggga ttggggggta cactgcaggg gagagactaa   4860
tagacatact agcatcacaa atacaaacaa cagaactaca aaaacaaatt ttaaaaatca   4920
acaattttcg ggtctattac agagatagca gagaccctat ttggaaagga ccggcacaac   4980
tcctgtggaa aggtgagggg gcagtagtca tacaagataa aggagacatt aaagtggtac   5040
caagaagaaa ggcaaaaata atcagagatt atggaaaaca gatggcaggt actgatagta   5100
tggcaaatag acagacagaa agtgaaagca tggaacagcc tggtgaaata ccataaatac   5160
atgtctaaga aggccgcgaa ctggcgttat aggcatcatt atgaatccag gaatccaaaa   5220
gtcagttcgg cggtgtatat tccagtagca gaagctgata tagtggtcac cacatattgg   5280
ggattaatgc caggggaaag agaggaacac ttgggacatg ggttagtat agaatggcaa   5340
tacaaggagt ataaaacaca gattgatcct gaaacagcag acaggatgat acatctgcat   5400
tatttcacat gttttacaga atcagcaatc aggaaggcca ttctagggca gagagtgctg   5460
accaagtgtg aatacctggc aggacatagt caggtaggga cactacaatt cttagccttg   5520
aaagcagtag tgaaagtaaa aagaaataag cctcccctac ccagtgtcca gagattaaca   5580
gaagatagat ggaacaagcc ctggaaaatc agggaccagc tagggagcca ttcaatgaat   5640
ggacactaga gctcctggaa gagctgaaag aagaagcagt aagacatttc cctaggcctt   5700
ggttacaagc ctgtgggcag tacatttatg agacttatgg agacacttgg gaaggagtta   5760
tggcaattat aagaatctta caacaactac tgtttaccca ttatagaatt ggatgccaac   5820
atagtagaat aggaattctc ccatctaaca caagaggaag aggaagaaga aatggatcca   5880
gtagatcctg agatgccccc ttggcatcac cctgggagca agccccaaac cccttgtaat   5940
aattgctatt gcaaaagatg ctgctatcat tgctatgttt gtttcacaaa gaagggtttg   6000
ggaatctccc atggcaggaa gaagcgaaga agaccagcag ctgctgcaag ctatccagat   6060
aataaagatc ctgtaccaga gcagtaagta acgctgatgc atcaagagaa cctgctagcc   6120
ttaatagctt taagtgcttt gtgtcttata aatgtactta tatggttgtt taaccttaga   6180
atttatttag tgcaaagaaa acaagataga agggagcagg aaatacttga aagattaagg   6240
agaataaagg aaatcaggga tgacagtgac tatgaaagta atgaagaaga acaacaggaa   6300
gtcatggagc ttatacatag ccatggcttt gctaatccca tgtttgagtt atagtaaaca   6360
```

-continued

```
attgtatgcc acagtttatt ctggggtacc tgtatgggaa gaggcagcac cagtactatt   6420
ctgtgcttca gatgctaacc taacaagcac tgaacagcat aatatttggg catcacaagc   6480
ctgcgttcct acagatccca atccacatga atttccacta ggcaatgtga cagataactt   6540
tgatatatgg aaaaattaca tggtggacca aatgcatgaa gacatcatta gtttgtggga   6600
acagagttta aagccttgtg agaaaatgac tttcttatgt gtacaaatga actgtgtaga   6660
tctgcaaaca aataaaacag gcctattaaa tgagacaata aatgagatga gaaattgtag   6720
ttttaatgta actacagtcc tcacagacaa aaaggagcaa aaacaggctc tattctatgt   6780
atcagatctg agtaaggtta atgactcaaa tgcagtaaat ggaacaacat atatgttaac   6840
taattgtaac tccacaatta tcaagcaggc ctgtcccaag gtaagttttg agcccattcc   6900
catacactat tgtgctccaa caggatatgc catctttaag tgtaatgaca cagactttaa   6960
tggaacaggc ctatgccaca atatttcagt ggttacttgt acacatggca tcaagccaac   7020
agtaagtact caactaatac tgaatgggac actctctaga gaaaagataa gaattatggg   7080
aaaaaatatt acagaatcag caaagaatat catagtaacc ctaaacactc ctataaacat   7140
gacctgcata agagaaggaa ttgcagaggt acaagatata tatacaggtc caatgagatg   7200
gcgcagtatg acacttaaaa gaagtaacaa tacatcacca agatcaaggg tagcttattg   7260
tacatataat aagactgtat gggaaaatgc cctacaacaa acagctataa ggtatttaaa   7320
tcttgtaaac caaacagaga atgttaccat aatattcagc agaactagtg gtggagatgc   7380
agaagtaagc catttacatt ttaactgtca tggagaattc ttttattgta acacatctgg   7440
gatgtttaac tatactttta tcaactgtac aaagtccgga tgccaggaga tcaaagggag   7500
caatgagacc aataaaaatg gtactatacc ttgcaagtta agacagctag taagatcatg   7560
gatgaaggga gagtcgagaa tctatgcacc tcccatcccc ggcaacttaa catgtcattc   7620
caacataact ggaatgattc tacagttaga tcaaccatgg aattccacag gtgaaaatac   7680
acttagacca gtagggggag atatgaaaga tatatggaga actaaattgt acaactacaa   7740
agtagtacag ataaaacctt ttagtgtagc acctacaaaa atgtcaagac caataataaa   7800
cattcacacc cctcacaggg aaaaaagagc agtaggattg ggaatgctat tcttggggggt   7860
gctaagtgca gcaggtagca ctatgggcgc agcggcaaca gcgctgacgg tacggaccca   7920
cagtgtactg aagggtatag tgcaacagca ggacaacctg ctgagagcga tacaggccca   7980
gcaacacttg ctgaggttat ctgtatgggg tattagacaa ctccgagctc gcctgcaagc   8040
cttagaaacc cttatacaga atcagcaacg cctaaaccta tggggctgta aaggaaaact   8100
aatctgttac acatcagtaa aatggaacac atcatggtca ggaagatata atgatgacag   8160
tatttgggac aaccttacat ggcagcaatg ggaccaacac ataaacaatg taagctccat   8220
tatatatgat gaaatacaag cagcacaaga ccaacaggaa aagaatgtaa aagcattgtt   8280
ggagctagat gaatgggcct ctctttggaa ttggtttgac ataactaaat ggttgtggta   8340
tataaaaata gctataatca tagtgggagc actaataggt ataagagtta ttatgataat   8400
acttaatcta gtgaagaaca ttaggcaggg atatcaaccc ctctcgttgc agatccctgt   8460
cccacaccgg caggaagcag aaacgccagg aagaacagga gaagaaggtg gagaaggaga   8520
caggcccaag tggacagcct tgccaccagg attcttgcaa cagttgtaca cggatctcag   8580
gacaataatc ttgtggactt accacctctt gagcaactta atatcaggga tccggaggct   8640
gatcgactac ctgggactgg gactgtggat cctgggacaa aagacaattg aagcttgtag   8700
```

-continued

```
actttgtgga gctgtaatgc aatattggct acaagaattg aaaaatagtg ctacaaacct   8760

gcttgatact attgcagtgt cagttgccaa ttggactgac ggcatcatct taggtctaca   8820

aagaatagga caaggattcc ttcacatccc aagaagaatt agacaaggtg cagaaagaat   8880

cttagtgtaa catggggaat gcatggagca aaagcaaatt tgcaggatgg tcagaagtaa   8940

gagatagaat gagacgatcc tcctctgatc ctcaacaacc atgtgcacct ggagtaggag   9000

ctgtctccag ggagttagca actagagggg gaatatcaag ttcccacact cctcaaaaca   9060

atgcagccct tgcattccta gacagccaca aagatgagga tgtaggcttc ccagtaagac   9120

ctcaagtgcc tctaaggcca atgaccttta aagcagcctt tgacctcagc ttctttttaa   9180

aagaaaaggg aggactggat gggttaattt actcccataa gagagcagaa atcctggatc   9240

tctggatata tcacactcag ggattcttcc ctgattggca gtgttacaca ccgggaccag   9300

gacctagatt cccactgaca tttggatggt tgtttaaact ggtaccagtg tcagcagaag   9360

aggcagagag actgggtaat acaaatgaag atgctagtct tctacatcca gcttgtaatc   9420

atggagctga ggatgcacac ggggagatac taaaatggca gtttgataga tcattaggct   9480

taacacatat agccctgcaa aagcacccag agctcttccc caagtaactg acactgcggg   9540

actttccaga ctgctgacac tgcggggact ttccagcgtg ggagggataa ggggcggttc   9600

ggggagtggc taaccctcag atgctgcata taagcagctg ctttccgctt gtaccgggtc   9660

ttagttagag gaccaggtct gagcccggga gctccctggc ctctagctga acccgctgct   9720

taacgctcaa taaagcttgc cttgagtgag aagcagtgtg tgctcatctg ttcaaccctg   9780

gtgtctagag atc                                                      9793
```

<210> SEQ ID NO 57
<211> LENGTH: 1733
<212> TYPE: DNA
<213> ORGANISM: Human immunodeficiency virus

<400> SEQUENCE: 57

```
aaacctccga cgcaacgggc tcggcttagc ggagtgcacc tgctaagagg cgagaggaac     60

tcacaagagg gtgagtaaat ttgctggcgg tggccagacc taggggaagg gcgaagtccc    120

taggggagga agatgggtgc gagagcgtct gtgttgacag ggagtaaatt ggatgcatgg    180

gaacgaatta ggttaaggcc aggatctaaa aaggcatata ggctaaaaca tttagtatgg    240

gcaagcaggg agctggaaag atacgcatgt aatcctggtc tattagaaac tgcagaaggt    300

actgagcaac tgctacagca gttagagcca gctctcaaga cagggtcaga ggacctgaaa    360

tctctctgga acgcaatagc agtactctgg tgcgttcaca acagatttga catccgagat    420

acacagcagg caatacaaaa gttaaaggaa gtaatggcaa gcaggaagtc tgcagaggcc    480

gctaaggaag aaacaagccc taggcagaca agtcaaaatt accctatagt aacaaatgca    540

cagggacaaa tggtacatca agccatctcc cccaggactt taaatgcatg ggtaaaggca    600

gtagaagaga aggcctttaa ccctgaaatt attcctatgt ttatggcatt atcagaaggg    660

gctgtcccct atgatatcaa taccatgctg aatgccatag gggacaccca aggggcttta    720

caagtgttga aggaagtaat caatgaggaa gcagcagaat gggatagaac tcatccacca    780

gcaatggggc cgttaccacc agggcagata agggaaccaa caggaagtga cattgctgga    840

acaactagca cacagcaaga gcaaattata tggactacta gaggggctaa ctctatccca    900

gtaggagaca tctatagaaa atggatagtg ctaggactaa acaaaatggt aaaaatgtac    960

agtccagtga gcatcttaga tattaggcag ggaccaaaag aaccattcag agattatgta   1020
```

-continued

```
gatcggtttt acaaaacatt aagagctgag caagctactc aagaagtaaa gaattggatg   1080

acagaaacct tgcttgttca gaattcaaac ccagattgta aacaaattct gaaagcatta   1140

ggaccagaag ctactttaga agaaatgatg gtagcctgtc aaggagtagg agggccaact   1200

cacaaggcaa aaatactagc agaagcaatg gcttctgccc agcaagattt aaaaggagga   1260

tacacagcag tattcatgca aagagggcag aatccaaata gaaaagggcc cataaaatgc   1320

ttcaattgtg gaaaagaggg acatatagca aaaaactgtc gagcacctag aaaaaggggt   1380

tgctggaaat gtggacagga aggtcaccaa atgaaagatt gcaaaaatgg aagacaggca   1440

aattttttag ggaagtactg gcctccgggg ggcacgaggc caggcaatta tgtgcagaaa   1500

caagtgtccc catcagcccc accaatggag gaggcagtga aggaacaaga gaatcagagt   1560

cagaaggggg atcaggaaga gctgtaccca tttgcctccc tcaaatccct ctttgggaca   1620

gaccaatagt cacagcaaag gttgggggtc atctatgtga ggctttactg gatacagggg   1680

cagatgatac agtattaaat aacatacaat tagaaggaag atggacacca aaa          1733
```

<210> SEQ ID NO 58
<211> LENGTH: 1733
<212> TYPE: DNA
<213> ORGANISM: Human immunodeficiency virus

<400> SEQUENCE: 58

```
aaacctccaa cgcaacgggc tcggcttagc ggagtgcacc tgctaagagg cgagaggaac     60

tcacaagagg gtgagtaaat ttgctggcgg tggccagacc taggggaagg gcgaagtccc    120

taggggagga agatgggtgc gagacggtct gtgttgacag ggagtaaatt ggatgcatgg    180

gaacgaatta ggttaaggcc aggatctaaa aaggcatata ggctaaaaca tttagtatgg    240

gcaagcaggg agctggaaag atacgcatat aatcctggtc tactagaaac tgcagaaggt    300

actgaacaac tgctacagca gttagagcca gctctcaaga cagggtcaga ggacctgaaa    360

tccctctgga acgcaatagc agtactctgg tgcgttcaca acagatttga catccgagat    420

acacagcagg caatacaaaa gttaaaggaa gtaatggcaa gcaggaagtc tgcagaggcc    480

gctaaggaag aaacaagctc aaggcaggca agtcaaaatt accctatagt aacaaatgca    540

cagggacaaa tggtacatca agccatatcc cctaggactt taaatgcatg ggtaaaggca    600

gtagaagaaa aggcctttaa ccctgaaatt attcctatgt ttatggcatt atcagaaggg    660

gctgtcccct atgatatcaa taccatgctg aatgccatag ggggacacca aggggcttta    720

caagtgttga aggaagtaat caatgaggaa gcagcagatt gggatagaac tcatccacca    780

gcaatggggc cgttaccacc agggcagata agggaaccaa caggaagtga cattgctgga    840

acaactagca cacagcaaga gcaaattata tggactacta gaggggctaa ctctatccca    900

gtaggagaca tctatagaaa atggatagtg ttaggactaa acaaaatggt aaaaatgtac    960

agtccagtga gcatcttaga tattaggcag ggaccaaaag aaccattcag agattatgta   1020

gatcggtttt acaaaacatt aagagctgag caagctactc aagaagtaaa gaattggatg   1080

acagaaaccc tcgttgttca gaattcaaac ccagattgta aacaaattct gaaagcatta   1140

ggaccaggag ctactttaga agaaatgatg gtagcctgtc aaggagtagg agggccaact   1200

cacaaggcaa aaatactagc agaagcaatg gcttctgccc agcaagattt aaagggagga   1260

tacacagcag tattcatgca aagagggcag aatccaaata gaaaagggcc tataaaatgt   1320

ttcaattgtg gaaaagaggg acatatagca aaaaactgtc gagcacctag aagaaggggt   1380
```

-continued tactggaaat gtggacagga aggtcaccaa atgaaagatt gcaaaaatgg aagacaggct 1440 attttttag ggaagtactg gcctccgggg ggcacgaggc cagccaatta tgtgcagaaa 1500
caagtgtccc catcagcccc accaatggag gaggcagtga aggaacaaga gaatcagaat 1560
caaaaggggg atcaggaaga gctgtaccca tttgcctccc tcaaatccct ctttgggaca 1620
gaccaatagt cacagcaaag gttgggggcc atctatgtga ggctttactg gatacagggg 1680
cagatgatac agtattaaat aacatacaat tagaaggaag atggacaccc aaa 1733

<210> SEQ ID NO 59
<211> LENGTH: 498
<212> TYPE: PRT
<213> ORGANISM: Human immunodeficiency virus

<400> SEQUENCE: 59

Met Gly Ala Arg Ala Ser Val Leu Thr Gly Ser Lys Leu Asp Ala Trp
1 5 10 15

Glu Arg Ile Arg Leu Arg Pro Gly Ser Lys Lys Ala Tyr Arg Leu Lys
20 25 30

His Leu Val Trp Ala Ser Arg Glu Leu Glu Arg Tyr Ala Cys Asn Pro
35 40 45

Gly Leu Leu Glu Thr Ala Glu Gly Thr Glu Gln Leu Leu Gln Gln Leu
50 55 60

Glu Pro Ala Leu Lys Thr Gly Ser Glu Asp Leu Lys Ser Leu Trp Asn
65 70 75 80

Ala Ile Ala Val Leu Trp Cys Val His Asn Arg Phe Asp Ile Arg Asp
85 90 95

Thr Gln Gln Ala Ile Gln Lys Leu Lys Glu Val Met Ala Ser Arg Lys
100 105 110

Ser Ala Glu Ala Ala Lys Glu Glu Thr Ser Pro Arg Gln Thr Ser Gln
115 120 125

Asn Tyr Pro Ile Val Thr Asn Ala Gln Gly Gln Met Val His Gln Ala
130 135 140

Ile Ser Pro Arg Thr Leu Asn Ala Trp Val Lys Ala Val Glu Glu Lys
145 150 155 160

Ala Phe Asn Pro Glu Ile Ile Pro Met Phe Met Ala Leu Ser Glu Gly
165 170 175

Ala Val Pro Tyr Asp Ile Asn Thr Met Leu Asn Ala Ile Gly Gly His
180 185 190

Gln Gly Ala Leu Gln Val Leu Lys Glu Val Ile Asn Glu Glu Ala Ala
195 200 205

Glu Trp Asp Arg Thr His Pro Pro Ala Met Gly Pro Leu Pro Pro Gly
210 215 220

Gln Ile Arg Glu Pro Thr Gly Ser Asp Ile Ala Gly Thr Thr Ser Thr
225 230 235 240

Gln Gln Glu Gln Ile Ile Trp Thr Thr Arg Gly Ala Asn Ser Ile Pro
245 250 255

Val Gly Asp Ile Tyr Arg Lys Trp Ile Val Leu Gly Leu Asn Lys Met
260 265 270

Val Lys Met Tyr Ser Pro Val Ser Ile Leu Asp Ile Arg Gln Gly Pro
275 280 285

Lys Glu Pro Phe Arg Asp Tyr Val Asp Arg Phe Tyr Lys Thr Leu Arg
290 295 300

Ala Glu Gln Ala Thr Gln Glu Val Lys Asn Trp Met Thr Glu Thr Leu
305 310 315 320

-continued

```
Leu Val Gln Asn Ser Asn Pro Asp Cys Lys Gln Ile Leu Lys Ala Leu
                325                 330                 335

Gly Pro Glu Ala Thr Leu Glu Glu Met Met Val Ala Cys Gln Gly Val
            340                 345                 350

Gly Gly Pro Thr His Lys Ala Lys Ile Leu Ala Glu Ala Met Ala Ser
        355                 360                 365

Ala Gln Gln Asp Leu Lys Gly Gly Tyr Thr Ala Val Phe Met Gln Arg
    370                 375                 380

Gly Gln Asn Pro Asn Arg Lys Gly Pro Ile Lys Cys Phe Asn Cys Gly
385                 390                 395                 400

Lys Glu Gly His Ile Ala Lys Asn Cys Arg Ala Pro Arg Lys Arg Gly
                405                 410                 415

Cys Trp Lys Cys Gly Gln Glu Gly His Gln Met Lys Asp Cys Lys Asn
            420                 425                 430

Gly Arg Gln Ala Asn Phe Leu Gly Lys Tyr Trp Pro Pro Gly Gly Thr
        435                 440                 445

Arg Pro Gly Asn Tyr Val Gln Lys Gln Val Ser Pro Ser Ala Pro Pro
    450                 455                 460

Met Glu Glu Ala Val Lys Glu Gln Glu Asn Gln Ser Gln Lys Gly Asp
465                 470                 475                 480

Gln Glu Glu Leu Tyr Pro Phe Ala Ser Leu Lys Ser Leu Phe Gly Thr
                485                 490                 495

Asp Gln


<210> SEQ ID NO 60
<211> LENGTH: 498
<212> TYPE: PRT
<213> ORGANISM: Human immunodeficiency virus

<400> SEQUENCE: 60

Met Gly Ala Arg Arg Ser Val Leu Thr Gly Ser Lys Leu Asp Ala Trp
  1               5                  10                  15

Glu Arg Ile Arg Leu Arg Pro Gly Ser Lys Lys Ala Tyr Arg Leu Lys
             20                  25                  30

His Leu Val Trp Ala Ser Arg Glu Leu Glu Arg Tyr Ala Tyr Asn Pro
         35                  40                  45

Gly Leu Leu Glu Thr Ala Glu Gly Thr Glu Gln Leu Leu Gln Gln Leu
     50                  55                  60

Glu Pro Ala Leu Lys Thr Gly Ser Glu Asp Leu Lys Ser Leu Trp Asn
 65                  70                  75                  80

Ala Ile Ala Val Leu Trp Cys Val His Asn Arg Phe Asp Ile Arg Asp
                 85                  90                  95

Thr Gln Gln Ala Ile Gln Lys Leu Lys Glu Val Met Ala Ser Arg Lys
            100                 105                 110

Ser Ala Glu Ala Ala Lys Glu Glu Thr Ser Ser Thr Gln Ala Ser Gln
        115                 120                 125

Asn Tyr Pro Ile Val Thr Asn Ala Gln Gly Gln Met Val His Gln Ala
    130                 135                 140

Ile Ser Pro Arg Thr Leu Asn Ala Trp Val Lys Ala Val Glu Glu Lys
145                 150                 155                 160

Ala Phe Asn Pro Glu Ile Ile Pro Met Phe Met Ala Leu Ser Glu Gly
                165                 170                 175

Ala Val Pro Tyr Asp Ile Asn Thr Met Leu Asn Ala Ile Gly Gly His
            180                 185                 190
```

-continued

```
Gln Gly Ala Leu Gln Val Leu Lys Glu Val Ile Asn Glu Glu Ala Ala
        195                 200                 205

Asp Trp Asp Arg Thr His Pro Pro Ala Met Gly Pro Leu Pro Pro Gly
    210                 215                 220

Gln Ile Arg Glu Pro Thr Gly Ser Asp Ile Ala Gly Thr Thr Ser Thr
225                 230                 235                 240

Gln Gln Glu Gln Ile Ile Trp Thr Thr Arg Gly Ala Asn Ser Ile Pro
                245                 250                 255

Val Gly Asp Ile Tyr Arg Lys Trp Ile Val Leu Gly Leu Asn Lys Met
            260                 265                 270

Val Lys Met Tyr Ser Pro Val Ser Ile Leu Asp Ile Arg Gln Gly Pro
        275                 280                 285

Lys Glu Pro Phe Arg Asp Tyr Val Asp Arg Phe Tyr Lys Thr Leu Arg
    290                 295                 300

Ala Glu Gln Ala Thr Gln Glu Val Lys Asn Trp Met Thr Glu Thr Leu
305                 310                 315                 320

Val Val Gln Asn Ser Asn Pro Asp Cys Lys Gln Ile Leu Lys Ala Leu
                325                 330                 335

Gly Pro Gly Ala Thr Leu Glu Glu Met Met Val Ala Cys Gln Gly Val
            340                 345                 350

Gly Gly Pro Thr His Lys Ala Lys Ile Leu Ala Glu Ala Met Ala Ser
        355                 360                 365

Ala Gln Gln Asp Leu Lys Gly Gly Tyr Thr Ala Val Phe Met Gln Arg
    370                 375                 380

Gly Gln Asn Pro Asn Arg Lys Gly Pro Ile Lys Cys Phe Asn Cys Gly
385                 390                 395                 400

Lys Glu Gly His Ile Ala Lys Asn Cys Arg Ala Pro Arg Arg Arg Gly
                405                 410                 415

Tyr Trp Lys Cys Gly Gln Glu Gly His Gln Met Lys Asp Cys Lys Asn
            420                 425                 430

Gly Arg Gln Ala Asn Phe Leu Gly Lys Tyr Trp Pro Pro Gly Gly Thr
        435                 440                 445

Arg Pro Ala Asn Tyr Val Gln Lys Gln Val Ser Pro Ser Ala Pro Pro
    450                 455                 460

Met Glu Glu Ala Val Lys Glu Gln Glu Asn Gln Asn Gln Lys Gly Asp
465                 470                 475                 480

Gln Glu Glu Leu Tyr Pro Phe Ala Ser Leu Lys Ser Leu Phe Gly Thr
                485                 490                 495

Asp Gln


<210> SEQ ID NO 61
<211> LENGTH: 35
<212> TYPE: PRT
<213> ORGANISM: Human immunodeficiency virus type 1

<400> SEQUENCE: 61

Arg Ile Leu Ala Val Glu Arg Tyr Leu Lys Asp Gln Gln Leu Leu Gly
  1               5                  10                  15

Ile Trp Gly Cys Ser Gly Lys Leu Ile Cys Thr Thr Ala Val Pro Trp
             20                  25                  30

Asn Ala Ser
         35


<210> SEQ ID NO 62
```

-continued

<211> LENGTH: 35
<212> TYPE: PRT
<213> ORGANISM: Human immunodeficiency virus

<400> SEQUENCE: 62

Arg Leu Gln Ala Leu Glu Thr Leu Ile Gln Asn Gln Gln Arg Leu Asn
1 5 10 15

Leu Trp Gly Cys Lys Gly Lys Leu Ile Cys Tyr Thr Ser Val Lys Trp
20 25 30

Asn Thr Ser
35

<210> SEQ ID NO 63
<211> LENGTH: 25
<212> TYPE: PRT
<213> ORGANISM: Human immunodeficiency virus

<400> SEQUENCE: 63

Trp Gly Ile Arg Gln Leu Arg Ala Arg Leu Gln Ala Leu Glu Thr Leu
1 5 10 15

Ile Gln Asn Gln Gln Arg Leu Asn Leu
20 25

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 64
ccataatatt cagcagaact ag 22

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 65
gctgattctg tataaggg 18

<210> SEQ ID NO 66
<211> LENGTH: 36
<212> TYPE: PRT
<213> ORGANISM: Human immunodeficiency virus type 1

<400> SEQUENCE: 66

Cys Thr Arg Pro Asn Asn Asn Thr Arg Lys Ser Ile Arg Ile Gln Arg
1 5 10 15

Gly Pro Gly Arg Ala Phe Val Thr Ile Gly Lys Ile Gly Asn Met Arg
20 25 30

Gln Ala His Cys
35

<210> SEQ ID NO 67
<211> LENGTH: 36
<212> TYPE: PRT
<213> ORGANISM: Human immunodeficiency virus type 2

-continued

```
<400> SEQUENCE: 67

Cys Lys Arg Pro Gly Asn Lys Ile Val Lys Gln Ile Met Leu Met Ser
  1               5                  10                  15

Gly His Val Phe His Ser His Tyr Gln Pro Ile Asn Lys Arg Pro Arg
             20                  25                  30

Gln Ala Trp Cys
        35
```